(12) United States Patent
Choi et al.

(10) Patent No.: US 11,542,180 B2
(45) Date of Patent: Jan. 3, 2023

(54) STERILIZING DEVICE

(71) Applicant: SEOUL VIOSYS CO., LTD., Gyeonggi-do (KR)

(72) Inventors: Jae Young Choi, Gyeonggi-do (KR); Shi Hyun Ahn, Gyeonggi-do (KR); Ki Yon Park, Gyeonggi-do (KR); Woong Ki Jeong, Gyeonggi-do (KR); Kyu Won Han, Gyeonggi-do (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 0 days.

(21) Appl. No.: 17/170,730

(22) Filed: Feb. 8, 2021

(65) Prior Publication Data
US 2021/0163316 A1 Jun. 3, 2021

Related U.S. Application Data

(63) Continuation of application No. PCT/KR2019/009934, filed on Aug. 8, 2019.

(30) Foreign Application Priority Data

Aug. 8, 2018 (KR) .................. 10-2018-0092397
Jan. 7, 2019 (KR) .................. 10-2019-0001944

(51) Int. Cl.
*C02F 1/32* (2006.01)

(52) U.S. Cl.
CPC ...... *C02F 1/325* (2013.01); *C02F 2201/3228* (2013.01)

(58) Field of Classification Search
CPC .. C02F 1/325; C02F 2201/3228; A61L 2/084; A61L 2/085; A61L 2/10
See application file for complete search history.

(56) References Cited

U.S. PATENT DOCUMENTS

| 8,658,101 | B1 | 2/2014 | Burnett |
| 9,295,741 | B2* | 3/2016 | Yerby ............ A61L 2/24 |
| 10,294,124 | B2 | 5/2019 | Khan et al. |
| 2012/0138545 | A1 | 6/2012 | Soler et al. |
| 2015/0165079 | A1 | 6/2015 | Shur et al. |
| 2015/0314024 | A1 | 11/2015 | Khan et al. |
| 2018/0257952 | A1* | 9/2018 | Wada ............ C02F 1/325 |

(Continued)

FOREIGN PATENT DOCUMENTS

| CN | 102486274 A | 6/2012 |
| CN | 107343243 A | 11/2017 |
| GB | 2531319 A | 4/2016 |

(Continued)

OTHER PUBLICATIONS

Extended European Search Report for European Application No. 19846864.7, dated Mar. 18, 2022, 6 pages.

(Continued)

*Primary Examiner* — Eliza W Osenbaugh-Stewart
(74) *Attorney, Agent, or Firm* — Perkins Coie LLP

(57) ABSTRACT

A sterilizing device includes a pipe having an inlet and an outlet and allowing fluid to move therethrough and a light source provided on one side of the pipe and providing light to the fluid. At least a portion of the pipe is provided in a spiral shape and the inlet and/or the outlet are arranged in a light emitting region.

20 Claims, 23 Drawing Sheets

(56) References Cited

U.S. PATENT DOCUMENTS

2020/0268918 A1* 8/2020 Nakamura ................ A61L 2/26

FOREIGN PATENT DOCUMENTS

| JP | 2016203095 | 12/2016 |
|----|------------|---------|
| KR | 1020150110083 | 10/2015 |
| KR | 1020170004157 | 1/2017 |
| KR | 2020170001535 | 5/2017 |

OTHER PUBLICATIONS

International Search Report for International Application PCT/KR2019/009934, dated Nov. 11, 2019.
Office Action for Chinese Application No. 201980002626.7, dated Jul. 25, 2022, 10 pages.

* cited by examiner

STERILIZING DEVICE

CROSS-REFERENCE OF RELATED APPLICATIONS AND PRIORITY

The Present application is a continuation application of International Application No. PCT/KR/2019/009934 filed Aug. 8, 2019 which claims priority to Korean Applications Nos. 10-2018-0092397 filed Aug. 8, 2018 and 10-2019-0001944 filed Jan. 7, 2019, the disclosures of which are incorporated by reference in their entirety.

TECHNICAL FIELD

Embodiment of the present invention relate to a sterilizing device and, more specifically to a sterilizing device adapted to emit light to a sterilization object for sterilization.

BACKGROUND

In recent years, pollution caused by industrialization, resulted in significant interest in the environment together with well-being trends. Demand for clean water or clean air has increased and is increasing, and various products such as water purifiers and air/water purifiers facilitating clean water and clean air are in demand.

SUMMARY

Embodiments of the present invention provide a sterilizing device capable of efficiently sterilizing a sterilization object.

In accordance with one aspect of the present invention, a sterilizing device includes: a pipe having an inlet and an outlet and adapted to deliver a fluid; and a light source provided to one side of the pipe and emitting light to the fluid, wherein at least part of the pipe has a spiral shape and at least one of the inlet and the outlet is disposed in a light emission region.

In at least one variant, at least part of the pipe may be transparent.

In another variant, one of the inlet and the outlet may correspond to a center of the spiral shape.

In yet another variant, the light source may include a substrate and at least one light emitting device disposed on the substrate.

In another variant, the pipe may be placed on a predetermined virtual plane. The virtual plane may be a flat surface.

In another variant, the plane may be parallel to the substrate.

In another variant, the inlet and the outlet may be placed at the same side as the plane.

In another variant, one of the inlet and the outlet may be placed at one side of the plane and the other may be placed at the other side of the plane.

In another variant, at least one of the inlet and the outlet may be placed in a direction parallel to the plane.

In another variant, the pipe may be placed on a certain virtual plane. The virtual plane may be an inner surface of a funnel shape.

In another variant, an angle defined between the inner surface of the funnel shape and an upper surface of the substrate may be in the range of 0 degrees to 20 degrees.

In another variant, the pipe may have flexibility.

In another variant, a line passing through a center of the pipe may be a curved line having a predetermined radius of curvature.

In another variant, a portion of the pipe may contact another portion of the pipe in plan view.

In another variant, a portion of the pipe may overlap another portion of the pipe in plan view.

In another variant, an area of the pipe in which a portion of the pipe overlaps another portion of the pipe may be 50% or less of an entire area of the pipe in plan view.

In another variant, the sterilizing device may further include a housing receiving the pipe and the light source. The sterilizing device may further include a cover fastened to the housing and covering the housing.

In another variant, at least one of the housing and the cover may have openings corresponding to the inlet and the outlet.

In accordance with another aspect of the present invention, the sterilizing device may be employed by a water supply including: a reservoir containing water; and a water treatment device connected to the reservoir and treating the water.

In accordance with a further aspect of the present invention, a sterilizing device may be provided in various forms and includes: a housing including a bottom and a sidewall extending upwards from the bottom and having an accommodation space defined by the bottom and the sidewall; a reflector disposed on the bottom and having a curved reflective surface protruding from the bottom; a support portion disposed on the reflector and having light transmittance; and a light emitting device disposed on the sidewall and emitting light, wherein, in a cross-section of the curved surface taken along a line perpendicular to the bottom and passing through a center of the bottom, a curved line corresponding to the curved surface corresponds to a portion of a parabolic line and a distance from the bottom to a focal point of the parabolic line may be greater than a distance from the bottom to a vertex of the curved reflective surface.

In at least one variant, the curved surface may have a vertex having the highest height from the center of the bottom in plan view.

In another variant, the curved surface may have a height gradually decreasing from the center of the bottom to an outside of the bottom.

In another variant, the reflector may have a smaller diameter than the bottom.

In another variant, the bottom may have a greater width than a height of the sidewall.

In another variant, the light emitting device may be provided in plural and may be disposed on the sidewall to emit light into the accommodation space.

In another variant, the sterilizing device may further include a blocking portion provided to an end of the sidewall distant from the bottom and blocking some of light emitted from the light emitting device.

In another variant, the blocking portion may be disposed along an edge of the bottom in plan view.

In another variant, the sterilizing device may further include a pipe disposed in the housing to be placed on a surface of the housing facing the bottom and adapted to deliver a fluid.

A distance from the bottom to a focal point of the parabolic line may be greater than a distance from the bottom to the pipe.

In another variant, a sterilization object to be sterilized by the light may be disposed to face the light emitting device, with the support portion interposed therebetween.

In one embodiment, the sterilization object may be a puff of a compact cosmetic. Embodiments of the present inven-

DETAILED DESCRIPTION OF EMBODIMENTS

Hereinafter, exemplary embodiments of the present invention will be described in detail with reference to the accompanying drawings so as to fully convey the spirit of the present invention to those skilled in the art.

Figure 1:
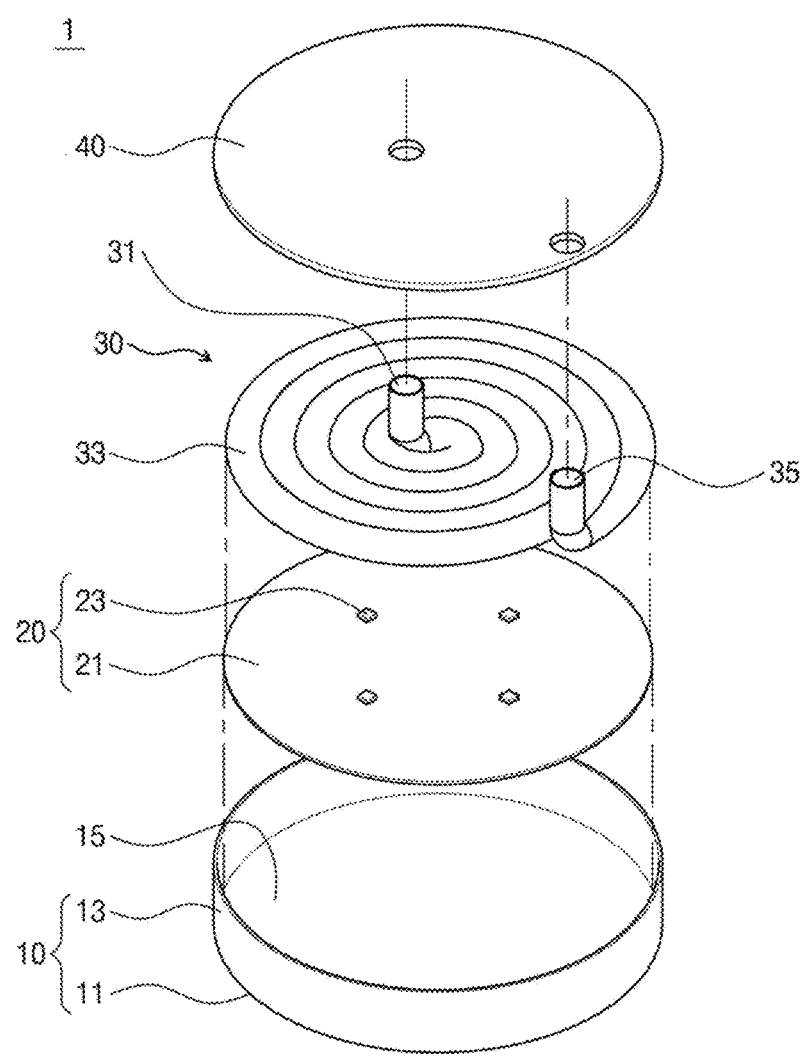
FIG. 1 is an exploded perspective view of a sterilizing device according to an embodiment of the present invention.
Figure 2:
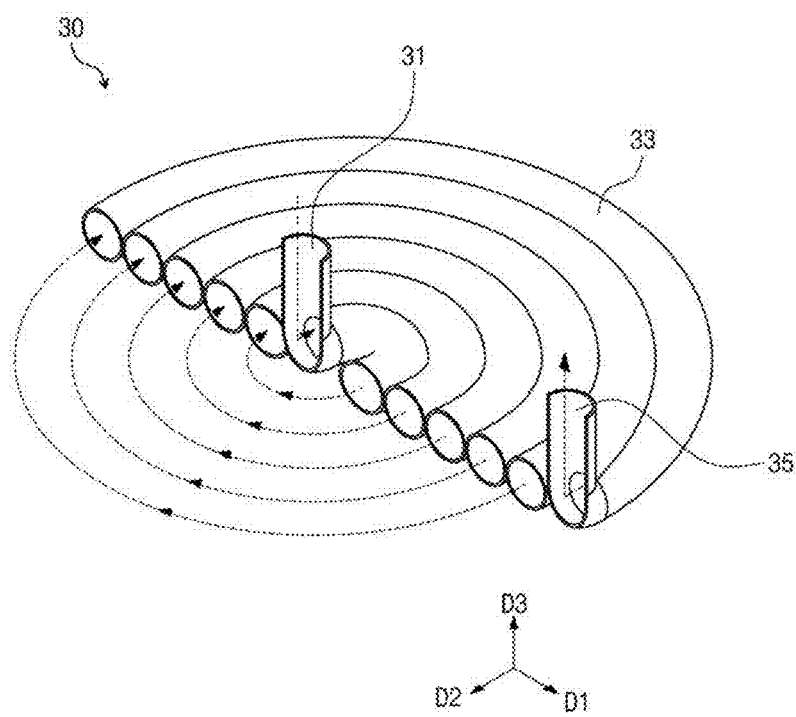
FIG. 2 is a perspective sectional view of a pipe of the sterilizing device according to the embodiment of the present invention.

FIG. 1 is an exploded perspective view of a sterilizing device according to an embodiment of the present invention and FIG. 2 is a perspective sectional view of a pipe of the sterilizing device according to the embodiment of the present invention.

In some embodiments, a variety of objects may be treated using a sterilizing device and may include a fluid, by way of example. The fluid may be water (especially running water) or air. In one embodiment, sterilization of a predetermined object includes, for example, sterilizing, purifying, and deodorizing the predetermined object through the sterilizing device. However, sterilization of a predetermined object is not limited thereto and may include other possible treatment carried out using a sterilizing device to be described later.

Herein, by way of example, a fluid will be described as a predetermined object.

Referring to FIG. 1 and FIG. 2, the sterilizing device 1 according to the embodiment of the present invention includes a housing 10 constituting an external appearance of the sterilizing device, a light source 20 disposed in the housing 10 and emitting light, a pipe 30 disposed in the housing 10 and adapted to deliver a fluid, and a cover 40 covering an upper side of the housing 10.

The light source 20 emits light toward the fluid flowing in the pipe 30. In one embodiment, the light source 20 may include a substrate 21 and at least one light emitting device 23 mounted on an upper surface of the substrate 21.

The substrate 21 may be realized by a plate and may have a circular shape corresponding to an outer spiral shape of the pipe 30. However, it should be understood that the shape of the substrate 21 is not limited thereto and may be modified in various ways so long as a suitable number of light emitting devices 23 can be efficiently mounted on the substrate 21.

The light emitting device 23 mounted on the upper surface of the substrate 21 may emit light at a predetermined irradiation angle in a direction substantially perpendicular to the upper surface of the substrate 21.

In some forms, the pipe 30 may have a hose shape extending in one direction and provides an inner space in which the fluid is treated. The fluid may flow in the inner space. The pipe 30 includes an inlet 31 through which the fluid flows into the pipe, an outlet 35 through which the fluid is discharged from the pipe, and a body 33 connecting the inlet 31 to the outlet 35.

The body 33 has a hollow pipe shape. The body 33 is open at opposite ends thereof in a longitudinal direction to have the inlet 31 and the outlet 35, respectively. In some forms, the body 33 may have a cylindrical shape. In this case, the body 33 has a circular cross-sectional shape, as taken in a direction perpendicular to a longitudinal direction of the cylindrical shape thereof. However, it should be understood that the body 33 is not limited thereto and, in other forms, may have various cross-sectional shapes, for example, an elliptical shape, a rectangular shape, and the like.

The pipe 30 is formed of a transparent insulating material to transmit light emitted from the light emitting devices 23. The pipe 30 may be formed of various materials without being limited to a particular material so long as the pipe has the functions mentioned above. For example, the pipe 30 may be formed of quartz or an organic polymer material that transmits light emitted from the light source 20. Here, as the organic polymer material has different absorption/transmission wavelengths depending on the type of monomer, a molding method, and conditions, the organic polymer material may be selected in consideration of wavelengths emitted from the light emitting devices 23. For example, organic polymers, such as poly(methyl methacrylate) (PMMA), polyvinyl alcohol (PVA), polypropylene (PP), and low-density polyethylene (PE) hardly absorb UV light, whereas organic polymers such as polyester can absorb UV light.

In at least one variant, a photocatalytic layer (not shown) including a photocatalytic material may be formed on inner and/or outer circumferential surfaces of the pipe 30. The photocatalytic material refers to a material causing catalytic reaction with light emitted from the light source 20 and may include titanium oxide ($TiO_2$), zinc oxide (ZnO), and tin oxide ($SnO_2$).

A photocatalyst can react with light in various wavelength bands depending on substances constituting the photocatalyst. In some forms, a material causing photocatalytic reaction with light in the UV wavelength band among various wavelength bands may be used. However, the photocatalyst is not limited thereto and other photocatalysts having the same or similar mechanism may be used depending on light emitted from the light source 20. The photocatalyst is activated by UV light to cause chemical reaction, thereby decomposing various pollutants and bacteria in air, which contacts the photocatalyst, through redox reaction. Air can be sterilized, purified, and deodorized through such photocatalytic reaction. In particular, upon sterilization, the photocatalyst provides a sterilization or antibacterial function by destroying enzymes in fungus cells and enzymes acting on the respiratory system are destroyed, thereby preventing growth of bacteria or fungi while decomposing toxins released therefrom.

The photocatalytic layer may be provided to any region of the pipe, which can receive the light emitted from the light source 20, and may be provided to an entire region or some region on the inner and/or outer circumferential surfaces of the pipe 30.

In some forms, the pipe 30, particularly, at least part of the body 33 of the pipe 30, may be provided in a spiral shape. Herein, the spiral shape refers to a shape of a curve winding around a central point such that a distance from the central point gradually increases.

As shown in FIG. 2, the body 33 of the pipe 30 may be placed in a spiral shape on a plane. Assuming that three directions of X, Y and Z axes orthogonal to one another are referred to as first to third directions D1, D2, D3, respectively, the body 33 of the pipe 30 may be placed on a plane defined by the first direction D1 and the second direction D2, that is, on an X-Y plane. In the following description, an upward direction means the third direction D3 and a downward direction means an opposite direction to the third direction D3.

In one embodiment, as shown in FIG. 1 and FIG. 2, the inlet 31 may be connected to one side of the body 33. An extension direction of the inlet 31 of the pipe 30 may be different from an extension direction of the body 33. In the embodiment, the extension direction of the inlet 31 may be inclined or perpendicular to the extension direction of the body 33, whereby the fluid can flow into the body 33 in the inclined direction or in the perpendicular direction thereto and can flow along the extension direction of the body 33. The fluid flowing into the body 33 through the inlet 31 is an object to be treated in the body 33, for example, an object to be sterilized, purified, or deodorized therein.

The outlet 35 may be disposed at a place spaced apart from the inlet 31 and may be connected to the body 33. In one embodiment, an extension direction of the outlet 35 may be inclined or perpendicular to the extension direction of the body 33, whereby the fluid can flow in the extension direction of the body 33 and can be discharged from the body 33 in the inclined direction or in the perpendicular direction thereto. The fluid discharged from the body 33 through the outlet 35 is an object treated in the body 33, for example, an object sterilized, purified, or deodorized therein.

The inlet 31 and the outlet 35 may be placed at the same side on the plane on which the pipe 30 is placed. Alternatively, the inlet 31 may be placed at one side on the plane on which the pipe 30 is placed and the outlet 35 may be placed at the other side on the plane on which the pipe 30 is placed. For example, all of the inlet 31 and the outlet 35 may be disposed in the third direction D3 (that is, in the Z-axis direction), Alternatively, the inlet 31 may be disposed in the third direction D3 and the outlet 35 may be disposed in an opposite direction to the third direction D3 (that is, in a −Z-axis direction). It should be understood that the locations of the inlet 31 and the outlet 35 may be modified in various ways depending on the housing 10 described below and an external apparatus for supplying a fluid.

It should be understood that the locations of the inlet 31 and the outlet 35 in the pipe 30 are not limited thereto and may be modified in various ways. For example, at least one of the inlet 31 and the outlet 35 may be disposed parallel to the plane on which the pipe 30 is placed. For example, in other embodiments, at least one of the inlet 31 and the outlet 35 may be disposed in the first direction D1 or in the second direction D2.

Each of the inlet 31 and the outlet 35 may have a circular or elliptical cross-sectional shape. However, it should be understood that the present invention is not limited thereto and each of the inlet 31 and the outlet 35 may have various cross-sectional shapes, for example, a polygonal cross-sectional shape. Here, the cross-section of each of the inlet 31 and the outlet 35 may refer to a cross-section taken in a direction intersecting the extension direction of the inlet 31 or a direction in which a fluid channel is formed.

Although not shown in the drawings, the inlet 31 and/or the outlet 35 may be provided with a separate pipe. The separate pipe may be connected to the inlet 31 and the outlet 35 through a nozzle. The nozzle may be coupled to the inlet 31 and/or the outlet 35 in various ways, for example, through screw coupling.

Figure 3:
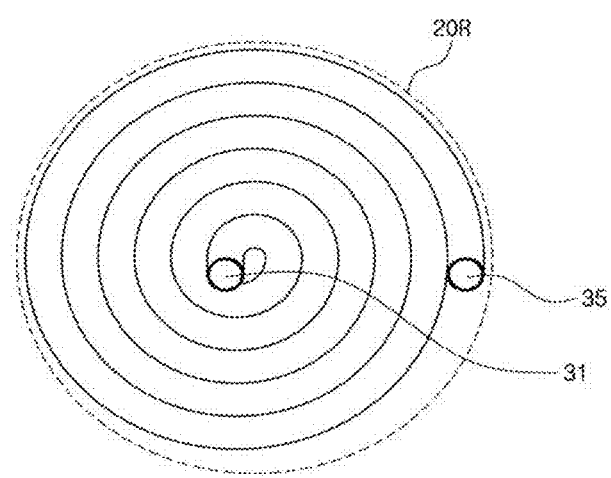
FIG. 3 is a plan view of the pipe of the sterilizing device shown in FIG. 2.

FIG. 3 is a plan view of the sterilizing device shown in FIG. 2, in which dark circles correspond to the inlet 31 and the outlet 35.

Referring to FIG. 2 and FIG. 3, in this embodiment, the inlet 31 may be disposed at the center of the spiral shape and the outlet 35 may be disposed outside the spiral shape in plan view. For the body 33 of the pipe 30 placed in a plane, all lines corresponding to axes of the pipe 30 are placed in the same plane and form a curved line having a predetermined radius of curvature.

In the embodiment, since the body 33 of the pipe 30 is disposed along a spiral, a portion of the pipe 30 becomes adjacent to another portion of the pipe 30. The adjacent portions of the pipe 30 may be separated from each other or contact each other. A distance between the adjacent portions of the pipe 30 may be generally constant.

In one embodiment, the body 33 of the pipe 30 may be disposed substantially in a light emission region 20R. In order to allow the fluid flowing in the pipe 30 to be irradiated with a sufficient quantity of light, at least part of the pipe 30 or, if possible, the entirety of the pipe 30, may be disposed in the light emission region 20R. The light emission region 20R may be determined based on the light emission angle of the light source 20, the quantity of light, the intensity of light, and the like.

In one embodiment, in order to ensure sufficient exposure to light, at least one of the inlet 31 and the outlet 35 may be disposed in the light emission region 20R. For example, both the inlet 31 and the outlet 35 or one of the inlet 31 and the outlet 35 may be disposed in the light emission region 20R. In this embodiment, both the inlet 31 and the outlet 35 may be disposed in the light emission region 20R such that the inlet 31 may correspond to the center of the spiral shape. In this structure, when flowing into the pipe through the inlet 31 disposed at the center of the spiral shape, the fluid sequentially flows along the spiral and is discharged through the outlet 35, whereby the fluid necessarily passes through the center of the spiral shape, at which the fluid is irradiated with a relatively large quantity of light having the highest intensity. Accordingly, the fluid can be sufficiently exposed to light even in consideration of the fact that the intensity or quantity of light can be changed depending on the location of the light emitting device 23.

In another embodiment, both the inlet 31 and the outlet 35 may be disposed in the light emission region 20R such that the outlet 35 may correspond to the center of the spiral shape. In this structure, when flowing into the pipe through the inlet 31 disposed outside the center of the spiral shape, the fluid flows along the spiral and is discharged through the outlet 35 disposed at the center of the spiral shape, whereby the fluid necessarily passes through the center of the spiral shape, at which the fluid is irradiated with a relatively large quantity of light having the highest intensity. Accordingly, the fluid can be sufficiently exposed to light even in consideration of the fact that the intensity or quantity of light can be changed depending on the location of the light emitting device 23.

However, it should be understood that the locations of the inlet 31 and the outlet 35 are not limited thereto. According to one embodiment, so long as the body 33 of the pipe 30 is irradiated with a sufficient quantity of light for sterilization, one of the inlet 31 and the outlet 35 may be disposed in the light emission region 20R and the other may be disposed outside the light emission region 20R. As one of the inlet 31 and the outlet 35 is disposed in the light emission region 20R, the fluid is discharged outside after passing through a portion at which the fluid is irradiated with a relatively large quantity of light having a relatively high intensity. As a result, the sterilization device can improve fluid treatment effects.

In some forms, the pipe 30 may have flexibility. Thus, the pipe 30 may be bent into a spiral shape. However, in other forms, the pipe 30 does not necessarily have flexibility and may be a non-flexible pipe bent into a spiral shape.

Figure 4A:
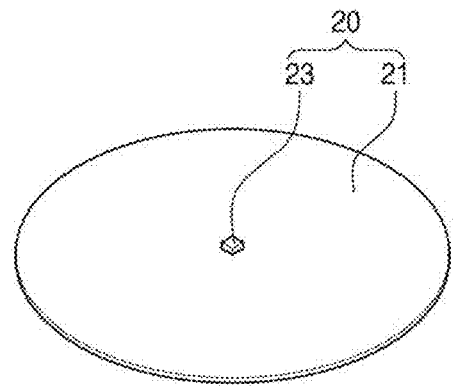
FIG. 4A is a perspective view of a light source in the sterilizing device according to the embodiment of the present invention.

As shown in FIG. 4A, the light source 20 is disposed at one side of the pipe 30 and emits light. In the embodiment in which the body 33 of the pipe 30 is disposed on a plane, the light source 20 may be disposed to allow light emitted from the light source 20 to reach the plane as much as possible. For example, the light source 20 is disposed in a direction in which the substrate 21 is parallel to the plane. Here, the light source 20 may be disposed to directly contact the pipe 30 or may be spaced apart from the pipe 30 so as to have a distance to allow light to be sufficiently dispersed.

In one embodiment, the light source 20 may be disposed to emit light in a substantially perpendicular direction to a flow direction of the fluid in the pipe 30. In this embodiment, an angle defined between the plane and light traveling perpendicular to the upper surface of the substrate 21 may be substantially about 90 degrees. However, it should be understood that the direction of light emitted from the light source 20 is not limited thereto and may be modified in various ways so long the body 33 of the pipe 30 can be irradiated with a sufficient quantity of light emitted from the light source 20 inclined at an angle within a predetermined range with respect to the flowing direction of the fluid.

Light emitted from the light source 20 may have various wavelength bands. Light emitted from the light source 20 may have wavelengths in the visible wavelength band, in the infrared (IR) wavelength band, or in other wavelength bands. In the embodiment, the light emitted from the light source 20 may have various wavelength bands depending on the type of fluid and an object to be treated (for example, germs or bacteria). In particular, when sterilizing a fluid, the light may have a sterilization wavelength band. For example, the light source 20 may emit light in the UV wavelength band.

In some forms, the light source 20 may emit light having a wavelength of about 100 nm to about 405 nm, which is a wavelength band capable of sterilizing microorganisms. For instance, the light source 20 may emit light having a wavelength of about 100 nm to about 280 nm; additionally, the light source 20 may emit light in a wavelength band of about 180 nm to about 280 nm, and as another example, the light source 20 may emit light having a wavelength of about 250 nm to about 260 nm. UV light in these wavelength bands has high sterilizing power and can destroy up to about 99% of bacteria, such as *Escherichia coli*, *Bacillus diphtheriae*, and *Bacillus dysenteriae*, at an intensity of, for example, 100 µW per $cm^2$. In addition, UV light in these wavelength bands can kill bacteria causing food poisoning, such as *Escherichia coli*, *Staphylococcus aureus*, *Salmonella* Weltevreden, *S. typhumurium*, *Enterococcus faecalis*, *Bacillus cereus*, *Pseudomonas aeruginosa*, *Vibrio parahaemolyticus*, *Listeria monocytogenes*, *Yersinia enterocolitica*, *Clostridium perfringens*, *Clostridium botulinum*, *Campylobacter jejuni*, and *Enterobacter sakazakii*.

To emit light as described above, the light source 20 may include at least one light emitting device 23. The light emitting device 23 is not limited to a particular kind so long as the light emitting device can emit light in a wavelength band capable of reacting with the photocatalytic material. For example, for the light source 20 emitting light in the UV wavelength band, the light source may employ various light emitting devices 23 configured to emit UV light. The light emitting device 23 configured to emit UV light may be, for example a light emitting diode. It should be understood that the light source 20 may employ other kinds of light emitting device 23 known in the art to emit light in other wavelength bands.

Figure 4B:
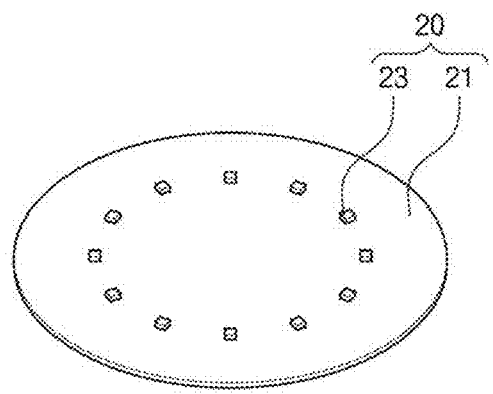
FIG. 4B is a perspective view of light sources having a circular arrangement in the sterilizing device.
Figure 4C:
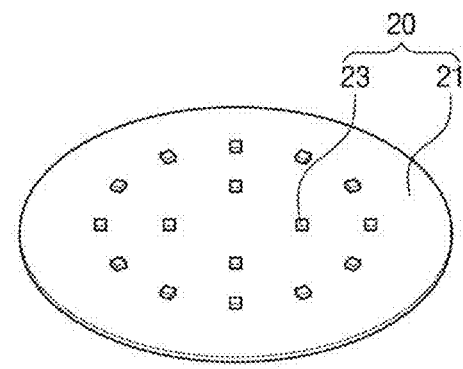
FIG. 4C is a perspective view of light sources having a different arrangement from the arrangement of FIG. 4B.

FIG. 4A to FIG. 4C are perspective views of the light source 20 in the sterilizing device according to the embodiment of the present invention. Although the substrate 21 may be provided with a withdrawal opening for withdrawal of a wire through which power is supplied to the light emitting device 23, the withdrawal opening is omitted in FIG. 4A to FIG. 4C for convenience of description.

Referring to FIG. 4A to FIG. 4C, the light emitting device 23 may be disposed in various numbers, for example, singularly or in plural, on the substrate 21. When the light emitting device 23 is provided in plural, the light emitting devices 23 are uniformly distributed on the substrate 21 such that the entirety of the pipe is uniformly irradiated with light. For example, for the substrate 21 constituted by n regions having the same area, each of first to $n^{th}$ regions may be provided with at least one light emitting device 23. When the substrate 21 has a circular shape or when the pipe has a circular cross-section and the substrate 21 does not have a circular shape, at least some of the light emitting devices 23 may be disposed equidistantly from the center of the circular shape or may be disposed at locations spaced apart therefrom by different distances. The light emitting devices 23 may be disposed at locations to ensure that light emitted therefrom uniformly reaches each region in the pipe.

For the light source 20 including multiple light emitting devices 23, each of the light emitting devices 23 may emit light in the same wavelength band or in different wavelength bands. For example, in one embodiment, each of the light emitting devices 23 may emit UV light in the same wavelength band or in similar wavelength bands. In another embodiment, some light emitting devices 23 may emit light in some UV wavelength bands and the other light emitting devices 23 may emit light in other UV wavelength bands.

When the light emitting devices 23 have different wavelength bands, the light emitting devices 23 may be arranged in various sequences. For example, a light emitting devices 23 emitting light in a first wavelength band and a light emitting devices 23 emitting light in a second wavelength band different from the first wavelength band may be alternately arranged.

Although not shown in FIGS. 4A through 4C, the sterilizing device according to the teachings of the present disclosure may further include a drive circuit connected to the light source 20 and an interconnect portion connecting the drive circuit to a light emitting device 23. The drive circuit may supply electric power to at least one light emitting device 23. For example, the drive circuit may be provided to the sterilizing device having the light source 20 to independently supply electric power to the light emitting devices 23. Accordingly, the light emitting devices 23 may be selectively driven such that all of the light emitting devices 23 can be turned on or off, or some light emitting devices 23 can be turned on, with the rest of the light emitting devices turned off.

Referring again to FIG. 1 to FIG. 3, the pipe 30 and the light source 20 may be received in the housing 10 having various shapes. The housing 10 generally constitutes an external appearance of the sterilizing device and has an accommodation space 15 that receives the pipe 30 and the light source 20 therein.

The housing 10 includes a bottom 11 and a sidewall 13 extending upwards from the bottom 11. The bottom 11 may have a shape corresponding to the shape of the light source 20 or the pipe 30. Thus, in the embodiment, the bottom 11 may have a circular shape in plan view. However, it should be understood that the shape of the bottom 11 is not limited thereto and may be modified according to the structure of the pipe 30. For example, the bottom 11 may have a rectangular shape and the sidewall 13 may have a sidewall corresponding to each side of the rectangle. In this case, the overall shape of the sterilizing device may be a rectangular parallelepiped.

The sidewall 13 may define the accommodation space 15 together with the bottom 11 and may have a height such that the light source 20, the pipe 30, and other components including wires can be sufficiently received in the accommodation space 15.

The cover 40 is disposed on an upper side of the housing 10. The cover 40 may be fastened to the sidewall 13 and covers an upper side of the accommodation space 15.

The cover 40 may be formed with openings at portions thereof corresponding to the inlet 31 and the outlet 35 of the pipe 30 such that the inlet 31 and the outlet 35 can be connected to the outside through the openings, as shown in FIG. 1. The inlet 31 and the outlet 35 may pass through the openings or may be connected thereto through a separate connection pipe 30 instead of passing through the openings. A fastener may be disposed between the housing 10 and the cover 40 to stably protect the pipe 30 and the light source 20.

It should be understood that the shapes of the housing 10 and the cover 40 are simplified for convenience of description and may be modified into various shapes. For example, although only the cover 40 is illustrated as having the openings corresponding to the inlet 31 and the outlet 35 in this embodiment, it should be understood that the present invention is not limited thereto. Alternatively, the housing 10 may be formed with at least one of the openings corresponding to the inlet 31 and the outlet 35.

In the embodiment, the housing 10 and the cover 40 may form the external appearance of the sterilizing device. In another embodiment, an additional component may be provided outside the housing 10 and the cover 40, and may constitute the external appearance of the sterilizing device.

In one embodiment, the housing 10 and the cover 40 may have a reflective layer therein. The reflective layer allows light emitted from the light source 20 to travel continuously inside the body 33 without leaking to the outside. The reflective layer may be formed of any material without limitation so long as the reflective layer can reflect light. In addition, the reflective layer may be formed in any region without limitation so long as light emitted from the light source 20 can reach the reflective layer, and may be formed in the entire region of the housing 10 and an inner surface of cover or may be formed in some regions thereof.

In one embodiment, the housing 10 and the cover 40 may be formed of a material having high reflectivity and/or a metal having high thermal conductivity such that light emitted from the light emitting device 23 can be efficiently reflected inside the pipe 30. For example, the pipe 30 may be formed of a material having high reflectivity, such as stainless steel, aluminum, magnesium oxide, and the like, or may be formed of a material having high thermal conductivity, such as stainless steel, aluminum, silver, gold, copper, and alloys thereof. Metals having high thermal conductivity can effectively dissipate heat from the pipe 30.

With the structure described above, the sterilizing device allows the fluid to flow along the body 33 having a spiral shape, thereby providing an elongated flow channel inside the pipe 30. The elongated flow channel inside the pipe 30 allows the fluid to be exposed to light emitted from the light emitting device 23 for a long period of time, thereby increasing the accumulation rate of light on the fluid while improving fluid treatment efficiency.

Further, according to the embodiments, since the fluid flows along the elongated flow channel inside the pipe 30, generation of an eddy can be minimized, thereby suppressing stagnation of the fluid that can occur near a portion where an eddy is generated. When some fluids are stagnant, the stagnant fluids and not the rest of fluids are exposed to light. However, the sterilizing device according to the embodiment provides the elongated flow channel that allows the fluids to be exposed to light.

Furthermore, according to the embodiments, since the sterilizing device has a first-in and first-out structure that allows the fluid first introduced into the pipe 30 to be eventually discharged first, the overall fluid can be uniformly exposed to light in the sterilizing device, thereby providing a uniform sterilization effect on the entire fluid.

Furthermore, as the substrate of the light source 20 is parallel to the arrangement direction of the pipe 30, most part of the body of the pipe 30 may be disposed close to the light source 20, and the distance from the substrate of the light source 20 to each portion of the pipe 30 is substantially the same or similar. The sterilization effect of light emitted from the light source 20 decreases with increasing distance from the light source to the pipe 30 to be sterilized, and the sterilization effect is increased with decreasing distance between the light source 20 and the pipe 30. In other words, since each portion of the pipe 30 is disposed at a close distance from the light source 20 as a whole in the sterilizing device, sterilization is performed within a distance where light emitted from the light source 20 has the maximum sterilization power. If the pipe 30 is distant from the substrate of the light source 20 as in the related art, some portion of the pipe 30 is close to the light source 20, but the other portion of the pipe 30 is distant from the light source 20. Thus, the sterilization device according to the teachings of the present disclosure can avoid a drawback of the related art, i.e., only some portion of the pipe 30 is sterilized within a distance where the light has high sterilization power.

Furthermore, since the light emitted from the light source 20 is provided to the fluid at an angle substantially close to 90 degrees, easy sterilization is achieved without light penetrating deeply into the fluid, thereby significantly improving sterilization efficiency of the light. If the fluid moves in a direction parallel to the light emitted from the light source 20, since a penetration depth of the light is not deep with respect to the flow direction of the fluid, sterilization occurs only in a direction in which the light source 20 is placed, and sterilization efficiency is very low in a portion of the pipe distant from the light source 20.

Furthermore, the light emitting devices 23 of the light source 20 may have a narrow beam angle of 90 degrees or a wide beam angle of 150 degrees or more. If the fluid flows in a direction parallel to the light emitted from the light source 20, there can be difficulty in sterilization using most light emitted widely at a wide beam angle. However, in the embodiments, since the pipe 30 is disposed on the plane facing the light source 20, the sterilization device advantageously allows the light emitted at a wide beam angle to be used as much as possible.

If a moving speed of the fluid in the pipe 30 is too low, the amount of the fluid to be treated becomes small. Thus, the moving speed of the fluid may be determined depending on capacity of the light emitting devices 23 treating the fluid in order to achieve effective treatment of a suitable amount of the fluid.

According to the teachings of the present disclosure, the pipe may have a variety of shapes so as to be sufficiently and efficiently exposed to light emitted from the light source.

Figure 5:
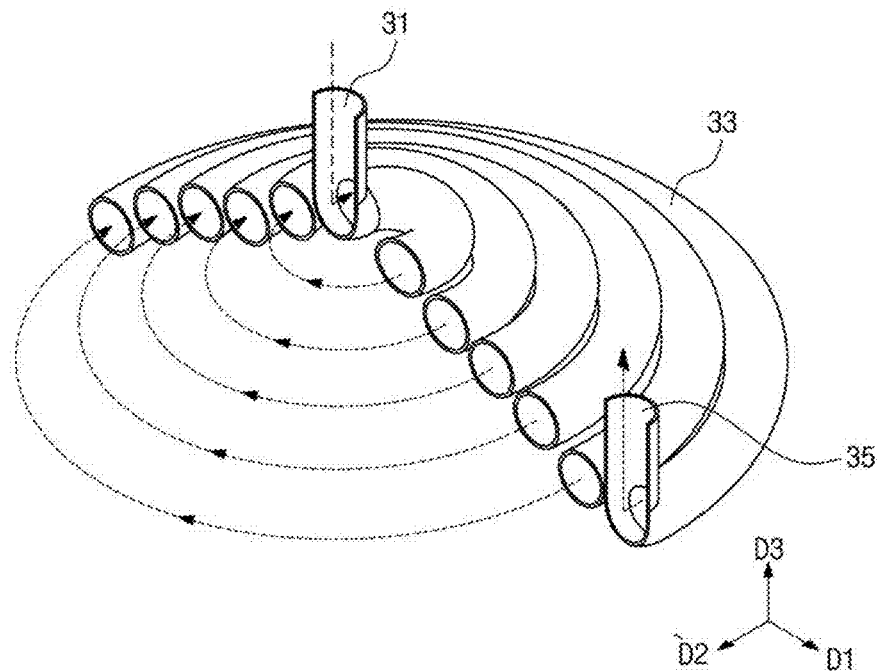
FIG. 5 is a perspective sectional view of a pipe of the sterilizing device according to the embodiment of the present invention.
Figure 6:
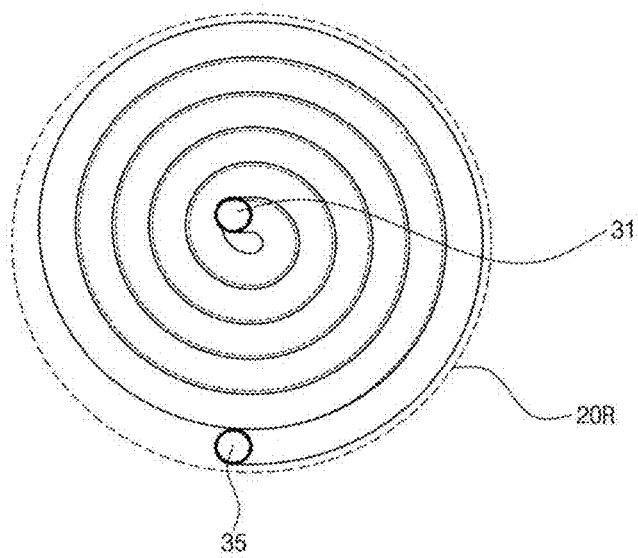
FIG. 6 is a plan view of the pipe of the sterilizing device shown in FIG. 5, in which dark circles correspond to an inlet and an outlet, respectively.

FIG. 5 is a perspective sectional view of the pipe of the sterilizing device according to the embodiment of the present invention and FIG. 6 is a plan view of the pipe of the sterilizing device shown in FIG. 5.

Referring to FIG. 5 and FIG. 6, in the sterilizing device according to the embodiment, the body 33 may be disposed in a spiral shape on a curved three-dimensional (3D) plane rather than on a two-dimensional (2D) plane. The body 33 may be disposed in a spiral shape on a virtual plane so as to have a shape that rises or descends in the third direction toward the center of the spiral shape. In this embodiment, the body 33 is illustrated as having a shape that rises in the third direction D3 toward the center of the spiral shape. In this structure, the virtual plane may be an inner surface of a funnel shape.

Here, an angle defined between the inner surface of the funnel shape and light emitted from the light source may be smaller than the angle therebetween when the body 33 has a flat shape. That is, this is because the inner surface of the funnel shape is inclined with respect to a plane perpendicular to the light emitted from the light source. As one example, the angle defined between the inner surface of the funnel shape and the light emitted from the light source may be 70 degrees to 90 degrees.

In this structure, when a portion of the body 33 is wound in a spiral shape on a 3D plane, the body 33 may be wound to have portions contacting each other with a height difference therebetween in plan view. When viewed in a 2D plane, a portion of the body 33 may overlap another portion of the body 33. When a portion of the body 33 overlaps another portion of the body 33, an overlapping area of the body 33 may be about 50% or less of the entire area of the body 33 in plan view. If the overlapping area of the body 33 exceeds about 50% of the entire area of the body 33, a sufficient amount of light may not reach the fluid. Thus, the body 33 may be wound so as to minimize the overlapping area.

In one embodiment, the body 33 may be inclined with respect to the light emitted from the light source 20 such that the flow channel of the fluid may be set at an angle optimized for a beam angle when a certain light emitting device 23 emits light at a large beam angle.

Further, although the body 33 is illustrated as having a shape extending in one direction in the above embodiment, the body 33 may have a different shape. Alternatively, a portion of the body may have a spiral shape in the light emission region, or at least one of the inlet 31 and the outlet 35 may be disposed in the light emission region 20R, as shown in FIG. 6.

In one embodiment, in a structure wherein the body 33 is disposed in a spiral shape on a curved 3D plane, a distance from the light source to the body 33 may vary depending on the location on the body 33. Accordingly, the quantity or intensity of light emitted from the light source and reaching each location on the body 33 may be different. In some embodiments, the shape of the light source may be changed to allow a sufficient quantity and intensity of light to reach each portion of the body 33, regardless of the location on the body 33. For example, the number or arrangement of light emitting devices in the light source may be changed, or the light emitting devices emitting different intensities of light may be combined in different combinations. As in this embodiment, when the body 33 is placed along the surface of the funnel shape, a portion of the body 33 placed at the center of the funnel is farther from the light source than a portion of the body 33 located outside the funnel shape. In this case, more light emitting devices may be placed at the center of the light source and fewer light emitting devices may be placed outside the light source, thereby uniformly providing a sufficient quantity of light to the entirety of the pipe.

Figure 7A:
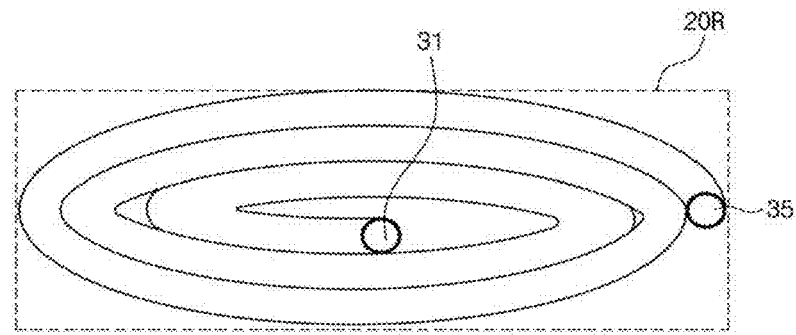
FIG. 7A is a plan view of modifications of the pipe in the sterilizing device according to the embodiment of the present invention, which have different light emission regions.
Figure 7B:
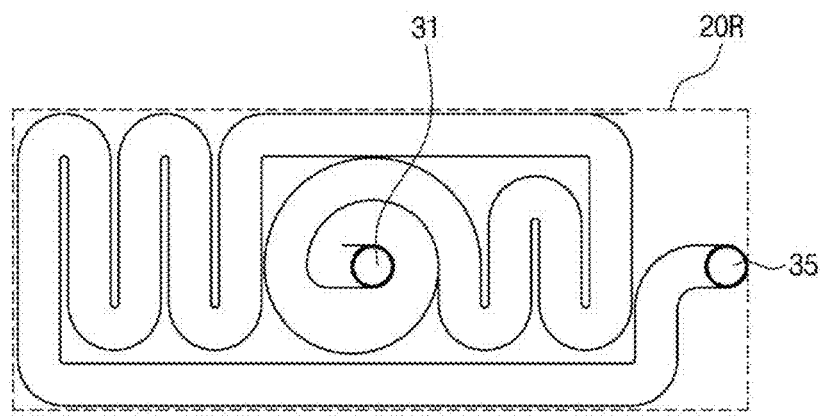
FIG. 7B is a plan view of another modifications of the pipe in the sterilizing device from those of FIG. 7A.
Figure 7C:
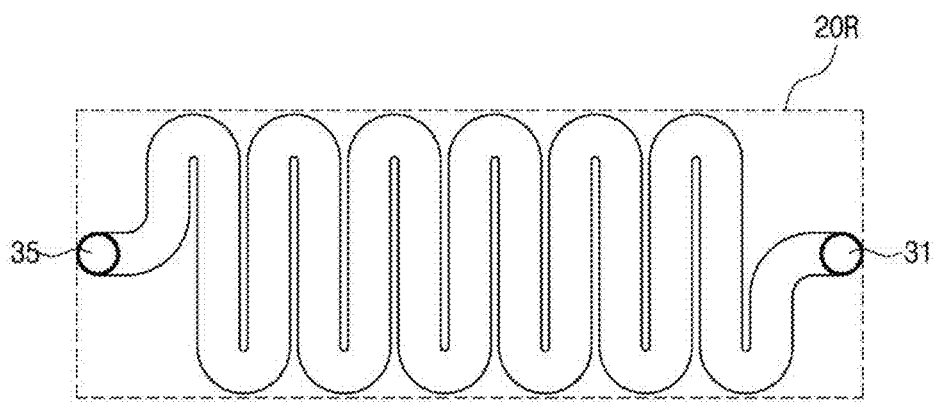
FIG. 7C is a plan view of different modifications of the pipe in the sterilizing device from those of FIG. 7B.

FIG. 7A to FIG. 7C are plan views of different modifications of the pipe 30 in the sterilizing device according to the embodiment of the present invention, which have different light emission regions 20R.

Referring to FIG. 7A to FIG. 7C, the light emission region 20R of the sterilizing device may have a circular shape as in the above embodiment, or may be provided in various forms, such as an elliptical shape, a semicircular shape, a polygonal shape, and various closed figures composed of curves and straight lines, instead of the circular shape. In these embodiments, the light emission region has a rectangular shape by way of example. In one embodiment, the light emission region 20R having a rectangular shape may be obtained by arranging multiple light emitting devices on a substrate having a substantially rectangular shape.

The pipe may be bent multiple times in various shapes so as to be exposed to as much light as possible corresponding to the shape of the light emission region. In particular, at least part of the pipe may be provided in a spiral shape, as shown in FIG. 7A and FIG. 7B, or the pipe may be bent multiple times in a zigzag shape, as shown in FIG. 7C. Here, as shown in FIG. 7A and FIG. 7B, both the inlet and the outlet may be disposed in the light emission region and may be disposed at the center of the light emission region.

With the structure described above, as in the embodiment described above, the flow channel of the fluid in the pipe has an elongated shape and is exposed to light emitted from the light emitting devices for a long period of time. As a result, the accumulation rate of light on the fluid is increased together with improvement in fluid treatment efficiency.

The fluid flows along the elongated pipe 30, generation of an eddy can be minimized, thereby suppressing stagnation of the fluid that can occur near a portion where an eddy is generated. Further, since the sterilizing device has a first-in and first-out structure that allows the fluid first introduced into the pipe to be eventually discharged first, the overall fluid can be uniformly exposed to light in the sterilizing device, thereby providing a uniform sterilization effect on the entire fluid. Furthermore, since the light emitted from the light source 20 is provided to the fluid at an angle substantially close to 90 degrees, easy sterilization is achieved without light penetrating deeply into the fluid. Furthermore, since the pipe is disposed on the plane facing the light source, the sterilization device advantageously allows light emitted at a wide beam angle to be used as much as possible.

Some components of the sterilizing device according to the teachings of the present disclosure may be modified to maximize sterilization efficiency with respect to a certain object.

Figure 8:
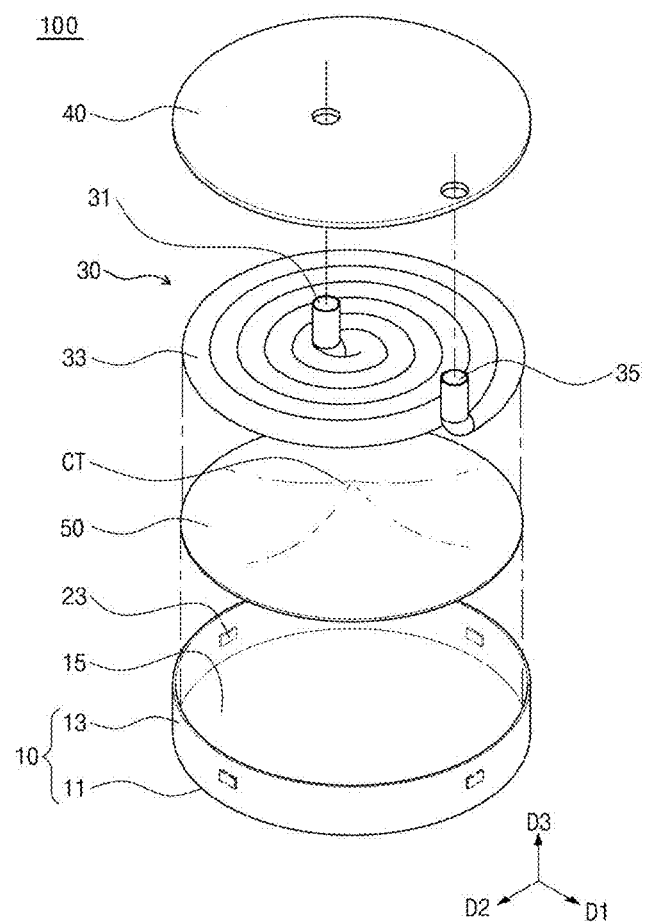
FIG. 8 is an exploded perspective view of a sterilizing device according to another embodiment of the present invention.

FIG. 8 is an exploded perspective view of a sterilizing device 100 according to another embodiment of the present invention. In this embodiment, the sterilizing device 100 refers to a device that performs treatment, such as sterilization, purification, and deodorization, for a predetermined object (or a sterilization object). The predetermined object may be a fluid (particularly, flowing water or air) that does not have a specific shape as in the above embodiments, or may be various objects having a specific shape, for example, parts in cosmetics, such as puffs and the like.

In the following embodiment, a fluid will be described as a predetermined object and the sterilizing device according to the embodiment of the invention is a fluid sterilizing device. However, the predetermined object may be changed in various ways without departing from the concept of the present invention. In addition, for convenience of description, the following description will focus on different features of the embodiment from the above embodiments and, for details of portions omitted herein, refer to the above description.

Referring to FIG. 8, the sterilizing device 100 according to another embodiment of the present disclosure includes a housing 10 constituting an external appearance of the sterilizing device 100, light emitting devices 23 disposed in the housing 10 and emitting light, a pipe 30 disposed in the housing 10 and adapted to deliver a fluid, a reflector 50 disposed in the housing 10 and reflecting light, and a cover 40 covering an upper side of the housing 10. The components of the sterilization device 10 may be structurally different from those of the sterilization device 1, but the same reference numerals are used to indicate the same components for convenience of descriptions.

The housing 10 defines an accommodation space 15 that receives the pipe 30, the reflector 50, and the light emitting devices 23, and includes a bottom 11 and a sidewall 13 extending upwards from the bottom 11. The accommodation space 15 may be defined by the bottom 11 and the sidewall 13 and may be open at an upper side thereof.

The bottom 11 may have a shape corresponding to the shape of the light emitting devices 23 or the pipe 30. Thus, in some forms, the bottom 11 may have a circular shape in plan view. However, it should be understood that the shape of the bottom 11 is not limited thereto and may be modified according to the structure of the pipe 30. In other forms, the bottom 11 may have a rectangular shape and the sidewall 13 may have a sidewall corresponding to each side of the rectangle. In this case, the overall shape of the sterilizing device may be a rectangular parallelepiped. In the following description of the embodiment, the bottom 11 having a circular shape will be described by way of example.

The sidewall 13 may define the accommodation space 15 together with the bottom 11 and may have a height such that the light emitting devices 23, the pipe 30, and other components including wires can be sufficiently received in the accommodation space 15.

In one embodiment, the bottom 11 may have a greater width than the height of the sidewall 13. For example, when the bottom 11 has a circular shape, the housing 10 may have a cylindrical shape having a smaller height than the diameter of the circle constituting the bottom 11.

The light emitting devices 23 are disposed on the sidewall 13 of the housing 10 and emit light into the accommodation space 15.

In some forms, the light emitting device 23 may be provided in plural. The light emitting device 23 may be provided in various numbers. For example, the housing may include 3, 4, 5 or 6 light emitting devices 23. When the light emitting device 23 is provided in plural, the light emitting devices 23 may be arranged in various ways so as to provide uniform light in the accommodation space 15. For example, the light emitting devices 23 may be radially arranged with respect to the center of the bottom 11. Further, the light emitting devices 23 may be arranged equidistantly from the center of the bottom 11 and may be arranged at constant intervals. As shown in the drawings, when the bottom 11 has a circular shape, the light emitting device 23 may be disposed at each vertex of a regular n-polygon inscribed within the circle. However, in one embodiment, when the light emitting devices 23 emit different intensities of light, the distance between the light emitting devices 23 may be set differently in consideration of the different intensities of light. Further, in the embodiment, the number of light emitting devices 23 may be changed depending upon the beam angle of each of the light emitting devices 23 and the light emitting devices 23 may be provided in a number that can cover about 90% or more of the light emission region when regions within the beam angles of the light emitting devices 23 are summed.

The light emitting devices 23 emit light towards the fluid flowing in the pipe 30. The light emitting devices 23 are disposed on the sidewall of the housing 10. Since the sidewall of the housing 10 extends upward from the bottom 11, light emitted from the light emitting devices 23 travels generally parallel to the bottom 11 of the housing 10 and then is directed upwards after being reflected directly by the accommodation space 15 or reflected multiple times by other components (by the reflector 50 or by the bottom 11 or the sidewall 13 of the housing 10) in the accommodation space.

Light emitted from the light emitting devices 23 may have various wavelength bands. The light emitted from the light emitting devices 23 may have wavelengths in the visible wavelength band, in the IR wavelength band, or in other wavelength bands. In the embodiment, the light emitted from the light emitting devices 23 may have various wavelength bands depending on the type of fluid and an object to be treated (for example, germs or bacteria). In particular, in fluid sterilization, the light may have a sterilization wavelength band.

A sterilization object is disposed in the accommodation space 15 of the housing 10 to be spaced apart from the light emitting devices 23. In this embodiment, the sterilization object is a fluid, which flows within the pipe 30 having the inlet and the outlet 35. In this embodiment, the fluid inside the pipe 30 is treated by applying light to the pipe 30. Accordingly, the pipe 30 will be described below as the sterilization object.

According to the embodiment, as the sterilization object, the pipe 30 is disposed on a surface inside the housing 10 to face the bottom 11. Here, the surface facing the bottom 11 is a virtual plane substantially parallel to the bottom 11. The virtual plane is spaced apart from the bottom 11 by a predetermined distance.

The pipe 30 may be secured to the housing 10 to be spaced apart from the bottom 11 and the reflector 50. To this end, the sidewall 13 of the housing 10 may be provided on an inner side thereof with a stepped portion, a fixing clip, or an engaging fastener to secure the pipe 30.

The pipe 30 has a hose shape extending in one direction. The fluid may flow in the pipe 30. The pipe 30 includes an inlet 31 through which the fluid flows into the pipe, an outlet 35 through which the fluid is discharged from the pipe, and a body 33 connecting the inlet 31 to the outlet 35.

The body 33 has a hollow pipe shape. The body 33 is open at opposite ends thereof in a longitudinal direction thereof to have the inlet 31 and the outlet 35, respectively.

The cover 40 may cover the accommodation space 15, which is open in the third direction D3, that is, in an upward direction. The cover 40 may be fastened to the sidewall 13 and covers an upper side of the accommodation space 15 in a downward direction.

The cover 40 may be formed with openings at portions thereof corresponding to the inlet 31 and the outlet 35 of the pipe 30 such that the inlet 31 and the outlet 35 can be connected to the outside through the openings. The inlet 31 and the outlet 35 may pass through the openings or may be connected thereto through a separate connection pipe 30 instead of passing through the openings. A fastener may be disposed between the housing 10 and the cover 40 to stably protect the pipe 30 and the light emitting devices 23.

It should be understood that the shapes of the housing 10 and the cover 40 are simplified for convenience of description and may be modified into various shapes. For example, although only the cover 40 is illustrated as having the openings corresponding to the inlet 31 and the outlet 35 in this embodiment, it should be understood that the present invention is not limited thereto. Alternatively, the housing 10 may be formed with at least one of the openings corresponding to the inlet 31 and the outlet 35.

In the embodiment, the housing 10 and the cover 40 may form the external appearance of the sterilizing device 100. In another embodiment, an additional component may be provided outside the housing 10 and the cover 40, and may form the external appearance of the sterilizing device.

The reflector 50 is disposed between the bottom 11 and the pipe 30 and reflects light emitted from the light emitting devices 23 such that the light can uniformly travel towards the pipe 30 as much as possible. To this end, the reflector 50 has a curved reflective surface protruding from the bottom 11 towards the pipe 30, that is, in the upward direction. Here, the reflector 50 protrudes in the upward direction and the curved reflective surface is downwardly concave.

The reflector 50 allows the light emitted from the light emitting devices 23 to travel continuously inside the body 33 without leaking to the outside. The reflector 50 may be formed of any material without limitation so long as the reflector 50 can reflect light.

The reflector 50 may be formed of a material having high reflectivity such that light emitted from the light emitting devices 23 can be efficiently reflected inside the pipe 30. In one embodiment, the reflector 50 may be formed of a material having high reflectivity, such as stainless steel, aluminum, magnesium oxide, and the like. Here, the reflector 50 may be realized by a monolithic structure formed of a material having high reflectivity, without being limited thereto. Alternatively, the reflector 50 may be formed of a material having relatively low reflectivity and coated with a material having high reflectivity.

In other embodiments, the housing 10 and the cover 40 may be formed of a material having high reflectivity such that light emitted from the light emitting devices 23 can be efficiently reflected inside the accommodation space 15 and finally reaches the pipe, and/or a metal having high thermal conductivity to allow heat generated from the light emitting devices 23 to be effectively discharged. For example, the housing 10 and the cover 40 may be formed of a material having high reflectivity, such as stainless steel, aluminum, magnesium oxide, and the like, or may be formed of a material having high thermal conductivity, such as stainless steel, aluminum, silver, gold, copper, and alloys thereof.

The sterilizing device according to the embodiment of the invention includes the reflector 50 to allow the light emitted from the light emitting devices 23 to be efficiently provided to the pipe 30 and the following description will focus on this feature.

Figure 9A:
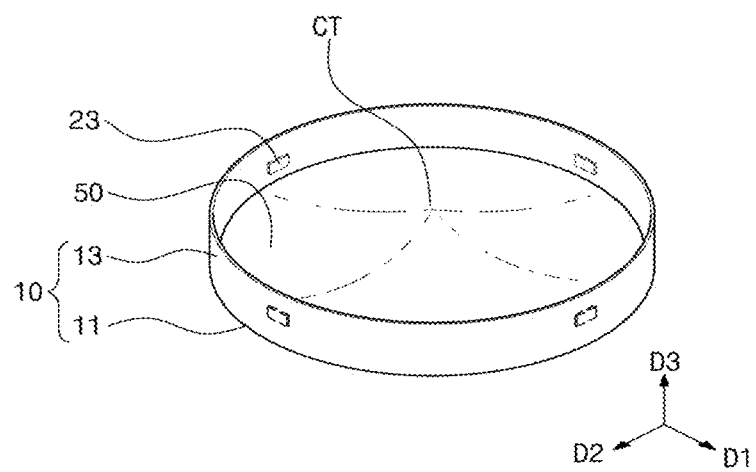
FIG. 9A is a perspective view of some portions of the sterilizing device according to the embodiment of the present invention, illustrating a housing, a reflector, and light emitting devices.
Figure 9B:
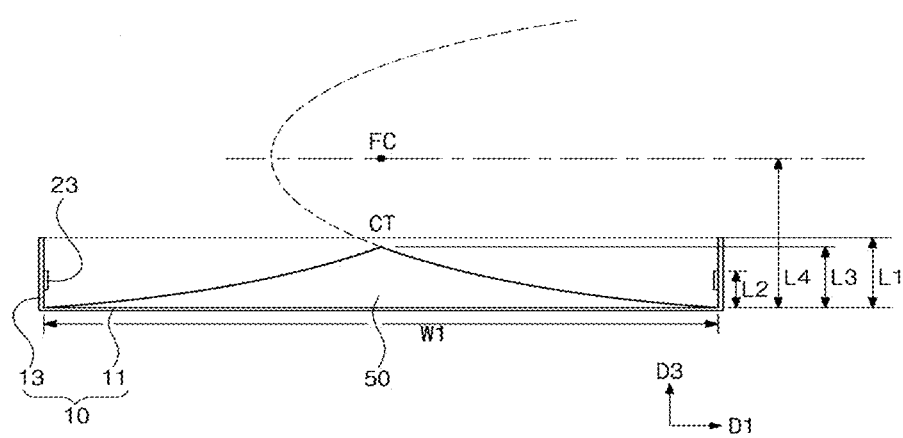
FIG. 9B is a sectional view of some portions of the sterilizing device of FIG. 9A.

FIG. 9A and FIG. 9B are a perspective view and a sectional view of a portion of a sterilizing device according to an embodiment of the invention, illustrating a housing, a reflector, and light emitting devices. In FIG. 9A and FIG. 9B, the cover and the pipe are omitted for convenience of description.

Referring to FIG. 9A and FIG. 9B, in the sterilizing device according to the embodiment of the invention, the bottom 11 of the housing 10 has a greater diameter than the height of the sidewall 13. Accordingly, the housing 10 has a cylindrical shape having a low height.

Assuming that the diameter of the bottom 11 of the housing 10 is a first diameter W1 and the height of the side wall extending upwards from an upper surface of the bottom 11 (that is, in the third direction D3) is a first height L1, the first diameter W1 may be greater than the first height L1, as shown in FIG. 9B.

The sidewall 13 may be provided with the light emitting devices 23, which may be placed at locations on the sidewall 13 corresponding to the second height L2 from the upper surface of the bottom 11. Here, for convenience of description, the height of the light emitting device 23 is represented by an upper height of the light emitting devices 23 from the bottom 11. The light emitting devices 23 are disposed on the sidewall 13 below an upper end of the sidewall 13. That is, the second height L2 at which the light emitting devices 23 are disposed is less than the first height L1 of the sidewall 13. Such a location of the light emitting devices 23 serves to separate the pipe 30 on the sidewall 13 from the light emitting devices 23 by a predetermined distance. If the distance between the pipe 30 and the light emitting devices 23 is too short, the light can be concentrated on some portion of the pipe 30. Thus, the second height L2 may be adjusted such that the pipe 30 is spaced apart from the light emitting devices 23 to achieve uniform application of light as much as possible.

The reflector 50 may have the same diameter W1 as the housing 10 and may have a shape protruding upwards from the bottom 11 of the housing 10. Assuming that a height of the highest portion of the reflector 50 protruding from the bottom 11 is a third height L3, the third height L3 may be less than the height L1 of the sidewall 13. In the embodiment, for the pipe 30 to be disposed inside the housing 10, it is desirable that the third height L3 be not greater than the first height L1.

Assuming that the highest portion of the reflector 50 is a vertex CT, the vertex CT may be disposed at the center of the bottom 11 in plan view. For example, if the bottom 11 has a circular or square shape, the vertex may be placed at the center of the circle or square when viewed in a plane. However, the vertex does not always have to be placed at the center of the bottom 11, and if the light emitting devices 23 spaced apart from each other emit light having different intensities, the location of the vertex may vary in consideration of the intensity of light emitted from the light emitting devices 23.

In this embodiment, the reflector 50 has a curved surface and gradually protrudes from the bottom 11 in a direction from an edge of the bottom 11 towards the center of the bottom 11. In other words, the curved surface has the highest vertex from the bottom 11 at the center of the bottom 11. In addition, the reflector 50 decreases in height from the bottom 11 from the vertex CT toward an edge of the reflector 50. In other words, the height of the reflector 50 from the bottom 11 decreases from the center toward the outside of the bottom 11.

In the embodiment, the reflector 50 has a curved shape optimized to allow light emitted from the light source to travel as uniformly as possible in the upward direction. To this end, in a cross-section of the curved surface of the reflector 50 taken along a line perpendicular to the bottom 11 and passing through the center of the bottom 11, a curved line corresponding to the cross-section of the curved surface may have various shapes. For example, the curved line corresponding to the cross-section of the curved surface may correspond to a portion of a parabolic line. The curved line may consist of only a portion corresponding to a parabolic line indicated by a single formula, or may consist of some portion corresponding to a parabolic line indicated by a certain formula, and the other portion corresponding to a parabolic line indicated by another formula.

Here, the axis of the parabolic line may be substantially parallel to the upper surface of the bottom 11, and a distance from the bottom 11 to a focal point FC of the parabolic line may be greater than a distance from the bottom 11 to the vertex CT. In other words, assuming that a height from the bottom 11 to the axis of the parabolic line is a fourth height L4, the fourth height L4 may be greater than the third height L3. Further, the height of the virtual plane, on which the pipe 30 is disposed, from the bottom 11 may be smaller than the distance from the bottom 11 to the focal point FC. If the distance from the bottom 11 to the focal point FC is less than or equal to the third height L3 and is less than or equal to the height of the virtual plane on which the pipe 30 is disposed, uniformity of light provided to the pipe 30 may not be guaranteed due to concentration of light caused by the intensity of light passing through the focal point FC.

In the embodiment, the shape of the parabolic line may be changed in various ways depending upon the number and locations of the light emitting devices 23, the width of the bottom 11, the height of the sidewall 13 and the like.

In the sterilizing device having the structure described above, since the light emitting devices 23 are disposed on the sidewall 13, most light emitted from the light emitting devices 23 travels substantially parallel to the bottom 11 and is applied to the pipe 30 through the reflector 50.

If the light emitting devices 23 are disposed on the bottom 11, light can travel upwards from the bottom directly below the pipe 30. When light is directly applied to the pipe 30 from such a close distance, a phenomenon in which the light is concentrated only at the locations of the light emitting devices 23 and less light is applied to the remaining region can occur. In other words, in the structure where the light emitting devices 23 are disposed directly on the bottom 11, the light emitting devices 23 emit light in a direction from the upper surface of the bottom 11 directly to the pipe 30. As a result, although the intensity of light applied to the pipe 30 can be sufficiently high, there can be a significant difference between the intensity of light in regions in which the light emitting devices 23 are disposed and the intensity of light in regions in which the light emitting devices 23 are not disposed. Accordingly, uniform treatment of the fluid flowing in the pipe 30 can be difficult in practice.

According to the embodiment, in order to prevent non-uniform application of light to the pipe 30, the light emitting devices 23 are disposed on the sidewall 13 of the housing 10 instead of being disposed directly below the pipe 30, that is, on the bottom 11. Here, the light emitting device 23 may be disposed on the sidewall 13. However, even when the light emitting devices 23 are simply placed on the sidewall 13, the phenomenon where light is concentrated on some portions of the pipe 30 corresponding to the regions in which the light emitting devices 23 are disposed is still present, and it is still difficult to ensure uniformity of light simply by placing the light emitting devices 23 on the sidewall 13.

Accordingly, in the sterilizing device according to the embodiment, instead of allowing direct irradiation of the pipe 30 with light emitted from the light emitting devices 23, the light emitting devices 23 are disposed to emit light parallel to the pipe 30 while the reflector 50 is disposed to uniformly reflect light towards the pipe 30, thereby improving efficiency in treatment of the pipe 30.

Further, in the sterilizing device according to the embodiment, although the light emitted from the light emitting devices 23 does not travel along the shortest distance, the distance between the light emitting device 23 and the pipe 30 may be maintained to secure the maximum sterilization power by the light emitted from the light emitting devices 23. Furthermore, since the light emitted from the light emitting devices 23 is provided to the pipe 30 over a very short distance, easy sterilization is achieved without light penetrating deeply into the fluid. As a result, sterilization efficiency of the light is significantly improved.

On the other hand, if the moving speed of the fluid in the pipe 30 is too low, the amount of the fluid to be treated becomes small. Thus, the moving speed of the fluid may be determined depending on capacity of the light emitting devices 23 treating the fluid in order to achieve effective treatment of a suitable amount of the fluid.

According to the embodiment, the sterilizing device allows the fluid to flow along the body 33 having a spiral shape, thereby providing an elongated flow channel inside the pipe 30. The elongated flow channel inside the pipe 30 allows the fluid to be exposed to the light emitted from the light emitting devices 23 for a long period of time, thereby increasing the accumulation rate of light on the fluid while improving fluid treatment efficiency.

Further, according to the embodiment, since the fluid flows along the elongated flow channel inside the pipe 30, generation of an eddy can be minimized, thereby suppressing stagnation of the fluid that can occur near a portion where an eddy is generated. When some fluids are stagnant, there can be a problem in that only the stagnant fluids are exposed to light. However, the sterilizing device according to the embodiment can solve this problem.

Furthermore, according to the embodiment, since the sterilizing device has a first-in and first-out structure that allows the fluid first introduced into the pipe 30 to be eventually discharged first, the overall fluid has an opportunity to be uniformly exposed to light in the sterilizing device, thereby providing a uniform sterilization effect on the entire fluid.

Although the fluid flowing in the pipe is illustrated as the sterilization object in the above embodiments, it should be understood that the sterilizing device according to the embodiment is not limited thereto.

Figure 10:
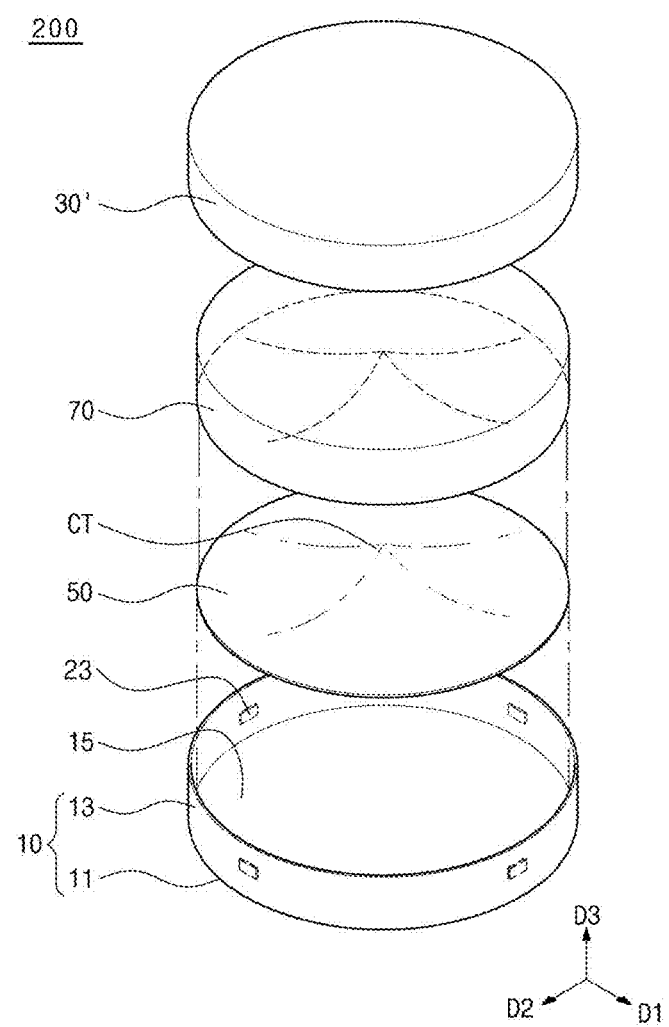
FIG. 10 is an exploded perspective view of a sterilizing device according to a further embodiment of the present invention.

FIG. 10 is an exploded perspective view of a sterilizing device according to a further another embodiment of the present invention.

Referring to FIG. 10, a sterilizing device 200 may be used to sterilize various portions of a sterilization object 30', for example, a surface of the sterilization object 30', by applying light to the surface thereof. In this case, some components such as a pipe, a cover, and the like, may be omitted and the sterilization object 30', that is, an article to be sterilized, may be directly disposed in the sterilizing device instead of the pipe. The sterilization object 30' may be disposed in the housing 10 described above, or may be disposed at any location without limitation so long as the light emitted from a light emitting device 23 can sufficiently reach the sterilization object 30', instead of being disposed in the housing. Although the sterilization object 30' has a flat cylindrical shape in this embodiment, it should be understood that the sterilization object 30' is not limited thereto and may have a different shape so long as the surface of the sterilization object 30' can be sterilized through application of light.

For example, the sterilization object 30' to be treated may be an article, such as a puff in a compact cosmetic. In this case, the housing 10 may correspond to a container for compact cosmetics and an article, such as a puff, may be disposed therein instead of the pipe, thereby enabling sterilization of the article. In the embodiment described above, since the pipe 30 (see FIG. 8) is secured to the sidewall 13 of the housing 10, the reflector 50 is spaced apart from the pipe 30 and air is interposed therebetween. However, in the sterilizing device according to this embodiment, a support portion 70 formed of a light-transmitting material may be further disposed between the reflector 50 and the sterilization object 30'.

The support portion 70 may include a light-transmitting material, for example, silicone or other light-transmitting polymer resins, and may be disposed on the reflector 50 to stably support the sterilization object 30' by filling a space of the reflector 50 with a material for the support portion 70 and then curing the material. In this case, the sidewall 13 of the housing 10 may not be provided with a device for securing the sterilization object 30'.

In the sterilizing device according to the embodiment, the reflector may be modified in various ways in order to improve treatment efficiency.

Figure 11A:
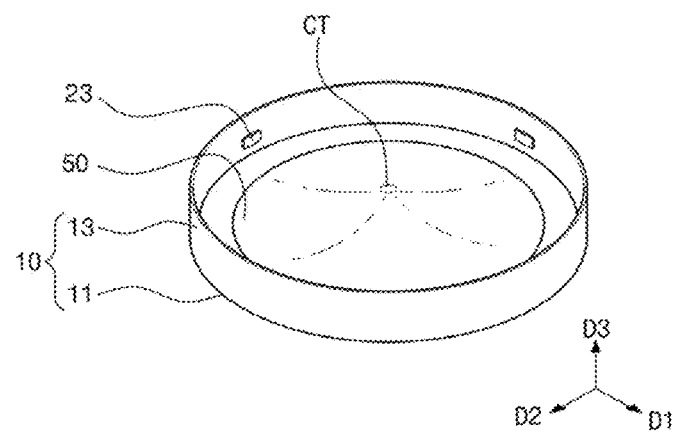
FIG. 11A is a perspective view of some portions of the sterilizing device according to the embodiment of the present invention, illustrating a housing, a reflector, and light emitting devices.
Figure 11B:
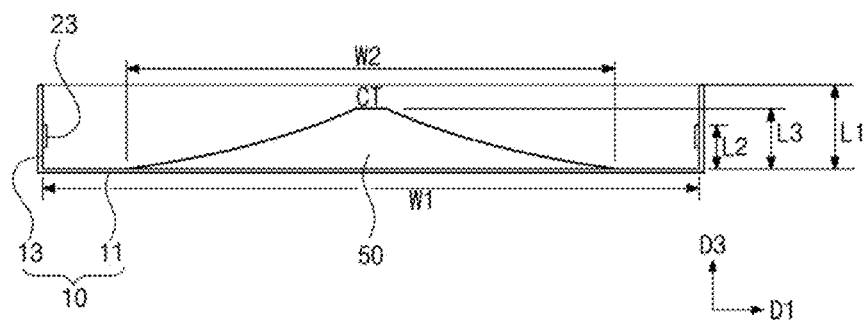
FIG. 11B is a perspective view of some portions of the sterilizing device of FIG. 11A.

FIG. 11A and FIG. 11B are a perspective view and a sectional view of a portion of a sterilizing device according to an embodiment of the invention, illustrating a housing, a reflector, and light emitting devices.

According to the embodiment, the reflector 50 may be disposed in various areas on the bottom 11. For example, the reflector 50 may be disposed in some regions on the bottom 11. A region in which the reflector 50 covers the bottom 11 may be modified in various ways depending on the location of the light emitting devices 23, the intensity of light emitted from the light emitting devices 23, the beam angle of the light emitted from the light emitting devices 23, and the like.

The reflector 50 may have various shapes. For example, for the bottom 11 having a circular shape in plan view, the reflector 50 may have a circular shape and may have a smaller diameter than the bottom 11. Assuming that the diameter of the bottom 11 is a first diameter W1 and the diameter of the reflector 50 is a second diameter W2, the second diameter W2 may be less than the first diameter W1.

When the bottom 11 and the reflector 50 have a circular shape, the bottom 11 and the reflector 50 may be concentrically disposed. Alternatively, in plan view, when the bottom 11 has a circular shape, the reflector 50 may have a different shape than the circular shape and may be realized by a protrusion or a recess formed towards the light emitting devices 23.

In the structure where the reflector 50 covers the entirety of the bottom 11, the quantity of light emitted from the light emitting device 23 and reflected upwards from the reflector 50 can be relatively increased. This is because the reflector 50 has a curved surface inclined with respect to a light emission direction, and this structure cannot sufficiently resolve concentration of light on the regions in which the light emitting devices 23 are disposed. In the structure where the reflector 50 covers a portion of the bottom 11, some fraction of the light emitted from the light emitting device 23 may be scattered and reflected by the bottom 11 and the other fraction of the light may be reflected upward by the curved surface of the reflector 50. As a result, compared with the structure where the reflector 50 covers the entirety of the bottom 11, this structure can relieve concentration of light and advantageously provides more uniform light to the pipe 30.

In some forms, the vertex of the reflector 50 may have a truncated conical shape and a top surface thereof may be parallel to the bottom 11. When the vertex of the reflector 50 is sharply formed in the form of an apex, light can be concentrated on the vertex. Thus, with the truncated conical shape of the reflector, it is possible to relieve concentration of light while improving overall uniformity of light.

In this embodiment, the height at which the light emitting devices 23 are disposed, that is, the second height L2, may be less than the height of the vertex of the reflector 50, that is, the third height L3, as shown in FIG. 11B. This is because the reflection effect by the reflector 50 cannot be achieved when the light emitting devices 23 are placed at a higher height than the second height L2.

In some forms, the sterilizing device may further include an additional component for uniform emission of light.

Figure 12A:
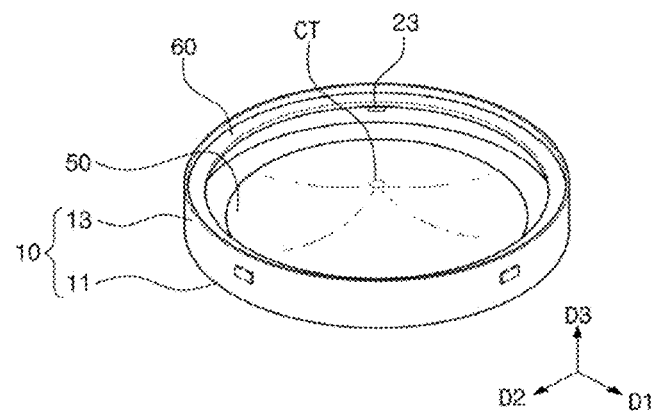
FIG. 12A is a perspective view of some portions of the sterilizing device according to the embodiment of the present invention, illustrating a housing, a reflector, light emitting devices, and a blocking portion.
Figure 12B:
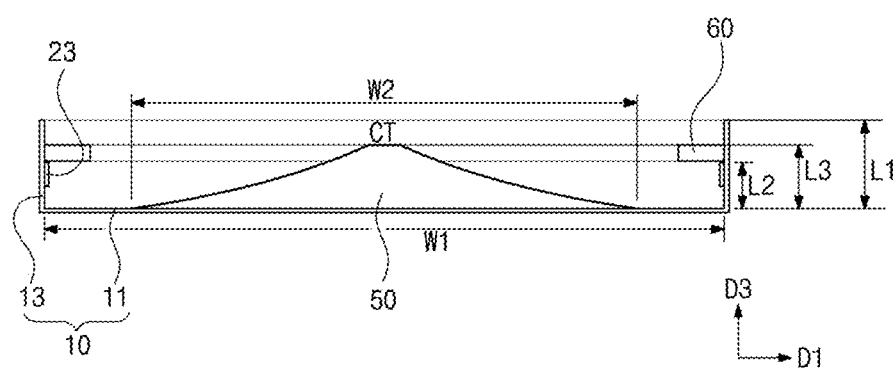
FIG. 12B is a sectional view of some portions of the sterilizing device of FIG. 12A.

FIG. 12A and FIG. 12B are a perspective view and a sectional view of a portion of a sterilizing device according to an embodiment of the invention, illustrating a housing, a reflector, light emitting devices, and a blocking portion.

In this embodiment, a blocking portion 60 may be disposed on the sidewall 13 to block some fraction of light emitted from the light emitting devices 23. The blocking portion 60 blocks light emitted from the light emitting devices 23 and traveling directly in the upward direction to minimize concentration of light on the regions in which the light emitting devices 23 are disposed. To this end, the blocking portion 60 is formed along the circumference of the sidewall 13 to be placed at an end of the sidewall 13 distant from the bottom 11 and protrudes from the sidewall 13 towards the accommodation space. As a result, the blocking portion 60 is disposed between the pipe and the light emitting devices 23 and prevents the light emitted from the light emitting devices 23 from traveling directly in the upward direction.

As compared with typical sterilizing devices, the sterilizing device according to the above embodiments significantly improves uniformity of light in the light emission region in which light is applied to the pipe. Hereinafter, light intensity distributions of sterilizing devices according to embodiments of the present disclosure will be compared with those of typical sterilizing devices. The following graphs depict the relative intensity of light (arbitrary unit) depending on a light emission region, and the horizontal axis and the vertical axis indicate distances from the center (mm).

Figure 13A:
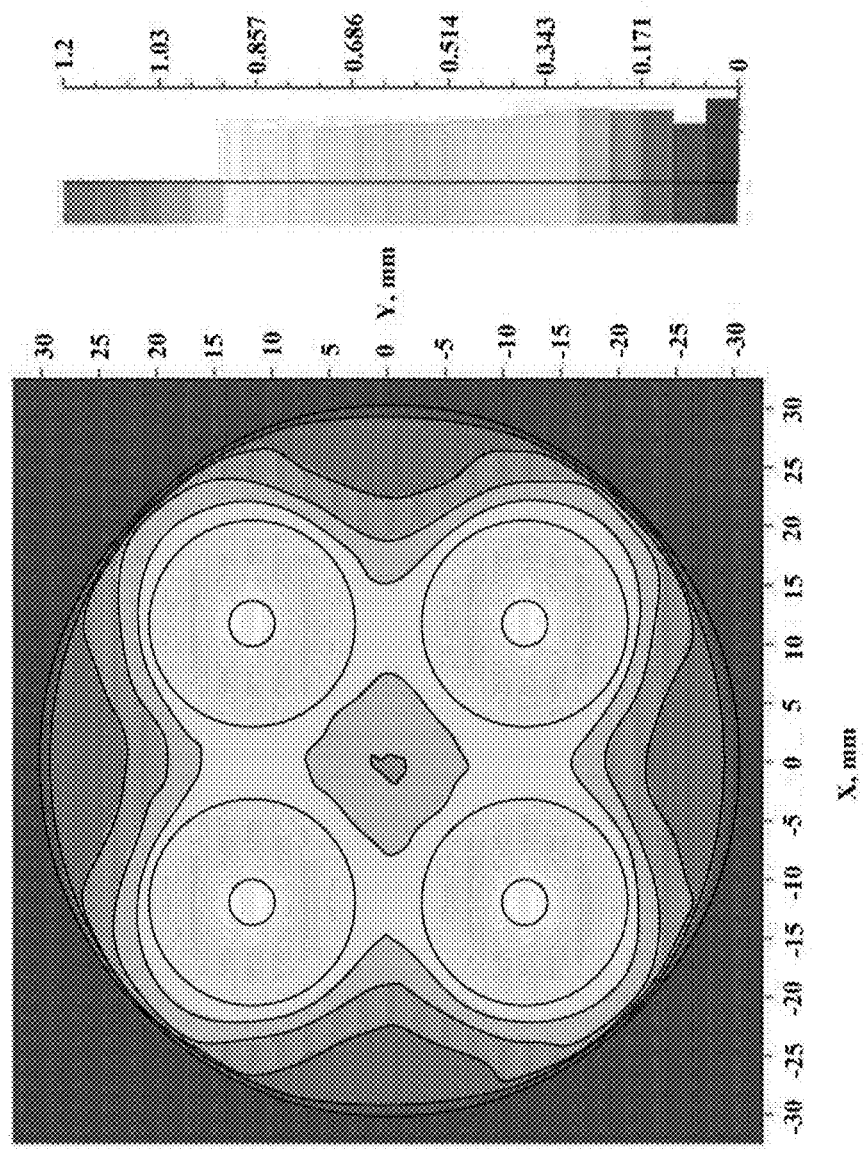
FIG. 13A is a graph depicting intensity distribution of light in use of a typical sterilizing device.
Figure 13B:
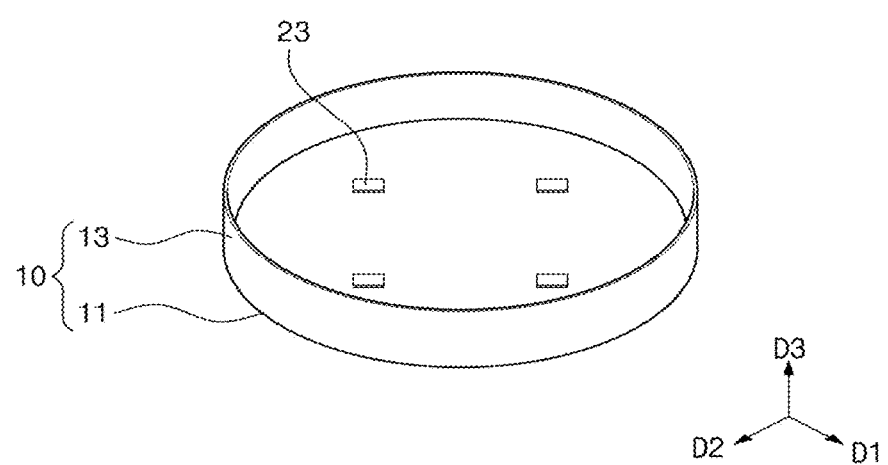
FIG. 13B is a view of some portions of the sterilizing device shown in FIG. 13A.

FIG. 13A is a graph depicting intensity distribution of light in use of a typical sterilizing device and FIG. 13B is a view of some portions of the sterilizing device shown in FIG. 13A. As can be seen from FIG. 13B, in the typical sterilizing device, four light emitting devices are disposed on the bottom of the housing.

Figure 14A:
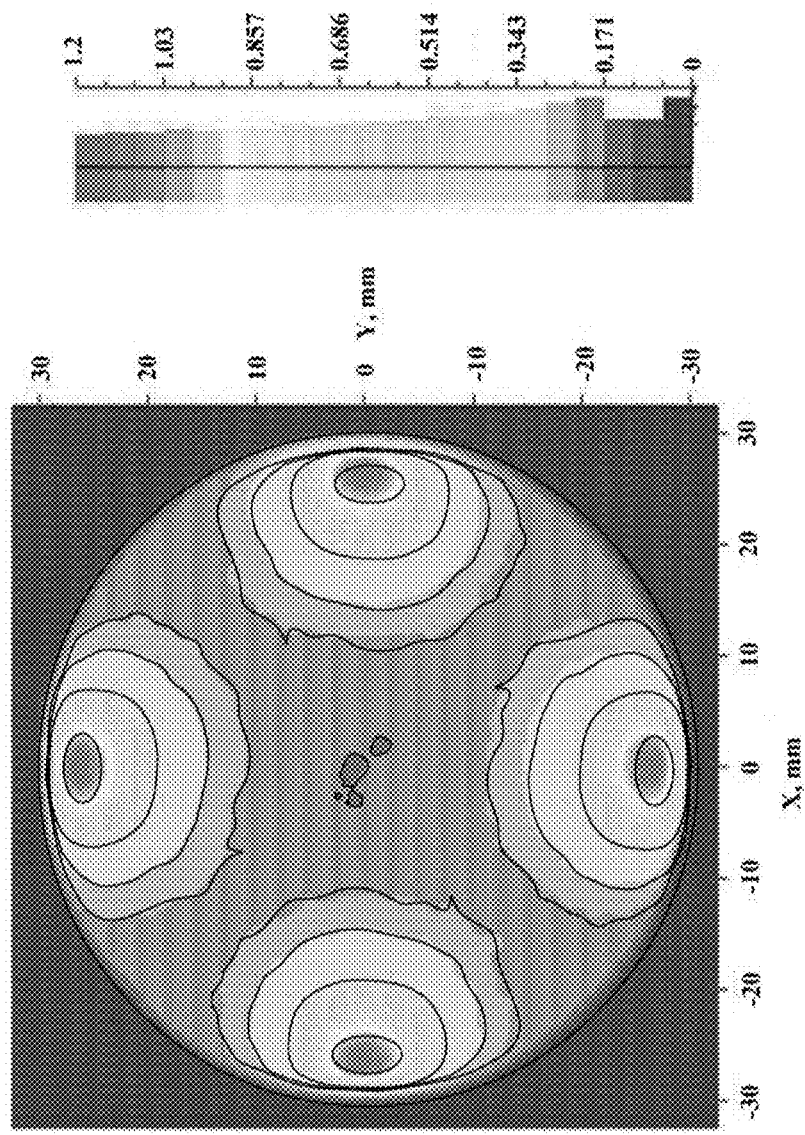
FIG. 14A is a graph depicting intensity distribution of light in use of another typical sterilizing device.
Figure 14B:
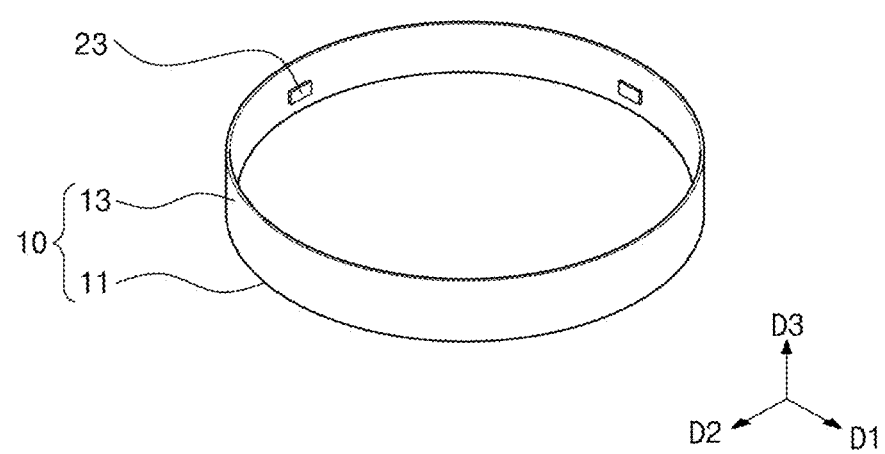
FIG. 14B is a view of some portions of the sterilizing device shown in FIG. 14A.

FIG. 14A is a graph depicting intensity distribution of light in use of another typical sterilizing device and FIG. 14B is a view of some portions of the sterilizing device shown in FIG. 14A. As can be seen from FIG. 14B, in this typical sterilizing device, four light emitting devices are arranged at constant intervals on the sidewall of the housing.

Figure 15A:
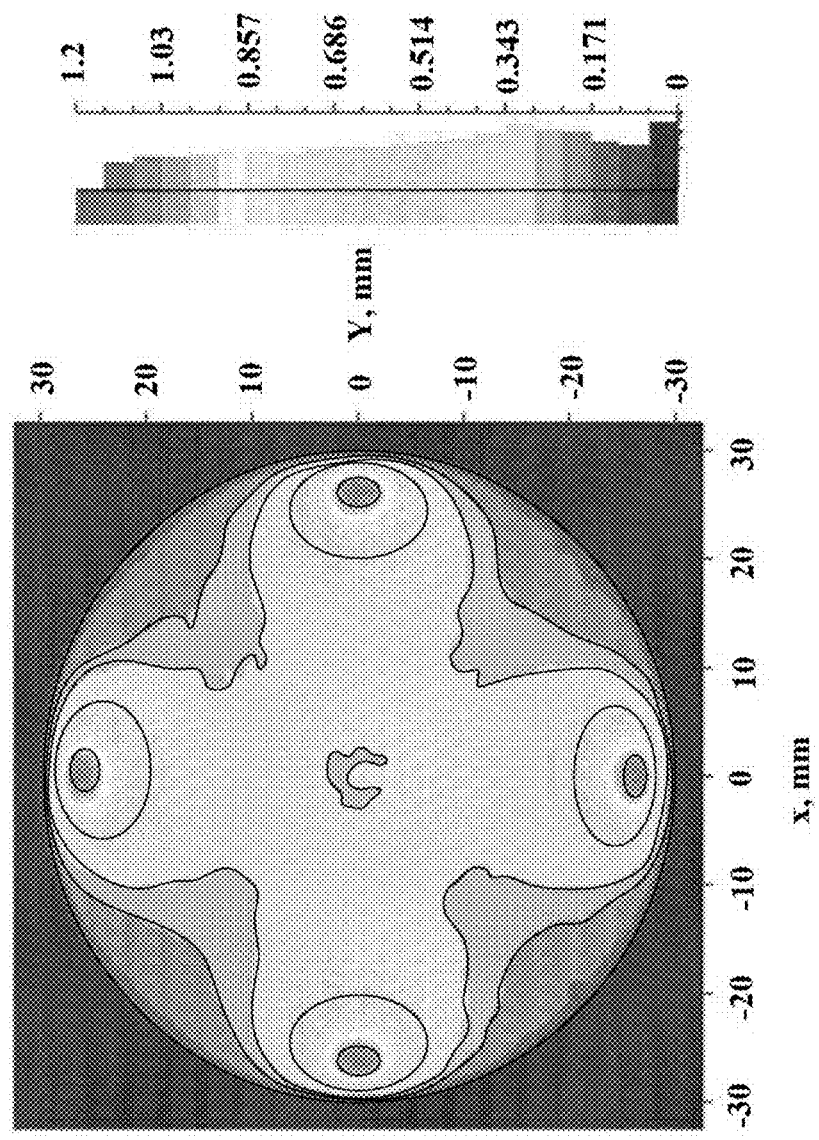
FIG. 15A is a graph depicting intensity distribution of light in use of a sterilizing device according to an embodiment of the present invention.
Figure 15B:
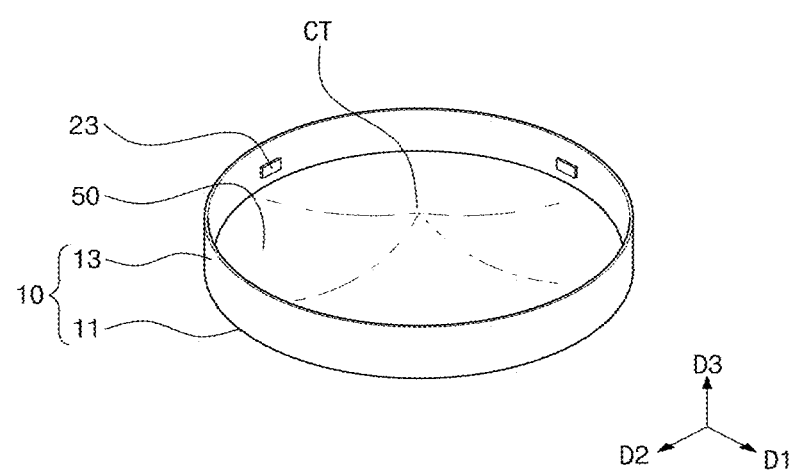
FIG. 15B is a view of some portions of the sterilizing device shown in FIG. 15A.

FIG. 15A is a graph depicting intensity distribution of light in use of a sterilizing device according to an embodiment of the present invention and FIG. 15B is a view of some portions of the sterilizing device shown in FIG. 15A. As can be seen from FIG. 15B, in the sterilizing device, the light emitting devices are disposed on the sidewall of the housing and the reflector is disposed on the bottom of the housing. Four (4) light emitting devices are disposed on the sidewall and the reflector covers the entirety of the bottom.

Figure 16A:
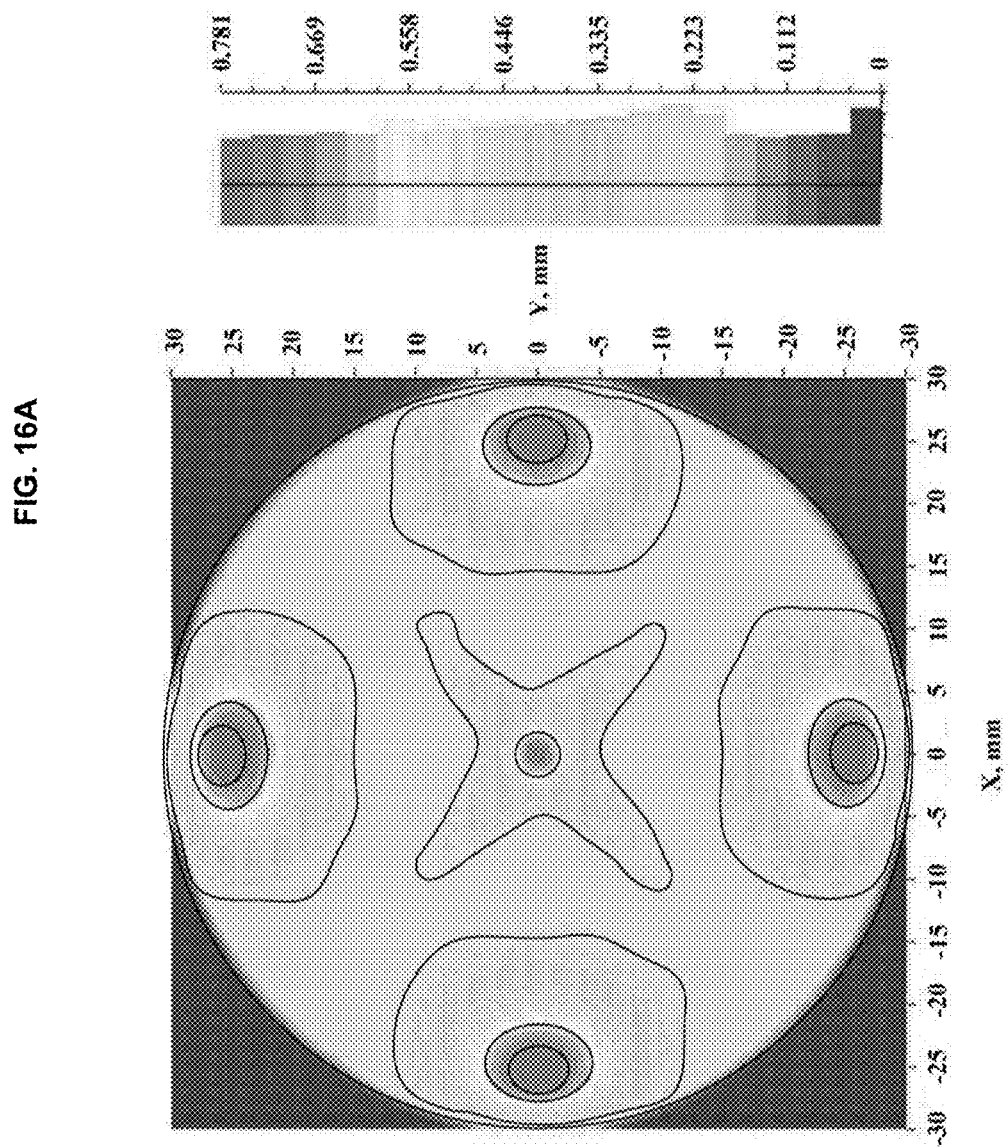
FIG. 16A is a graph depicting intensity distribution of light in use of a sterilizing device according to an embodiment of the present invention.
Figure 16B:
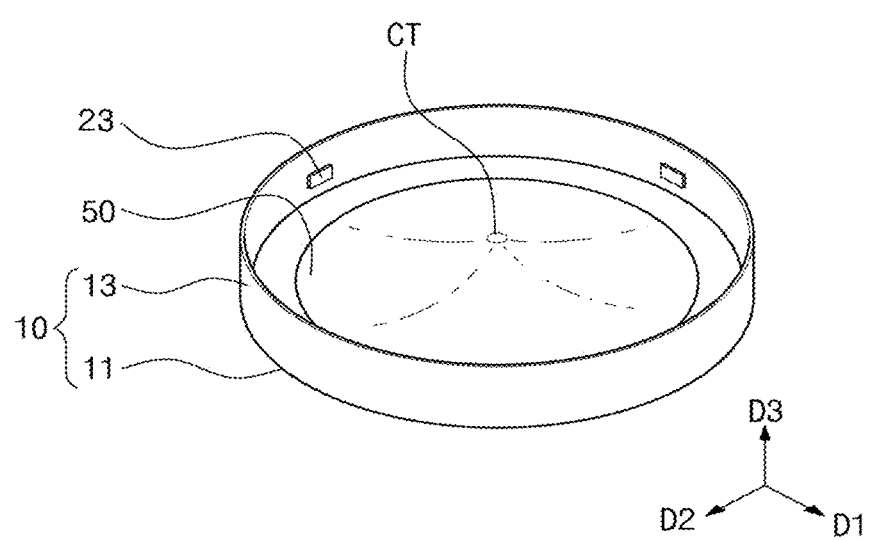
FIG. 16B is a view of some portions of the sterilizing device shown in FIG. 16A.

FIG. 16A is a graph depicting intensity distribution of light in use of a sterilizing device according to an embodiment of the present invention and FIG. 16B is a view of some portions of the sterilizing device shown in FIG. 16A. As can be seen from FIG. 16B, in the sterilizing device, the light emitting devices are disposed on the sidewall of the housing and the reflector is disposed on the bottom of the housing. Four (4) light emitting devices are disposed on the sidewall and the reflector covers a portion of the bottom.

Figure 17A:
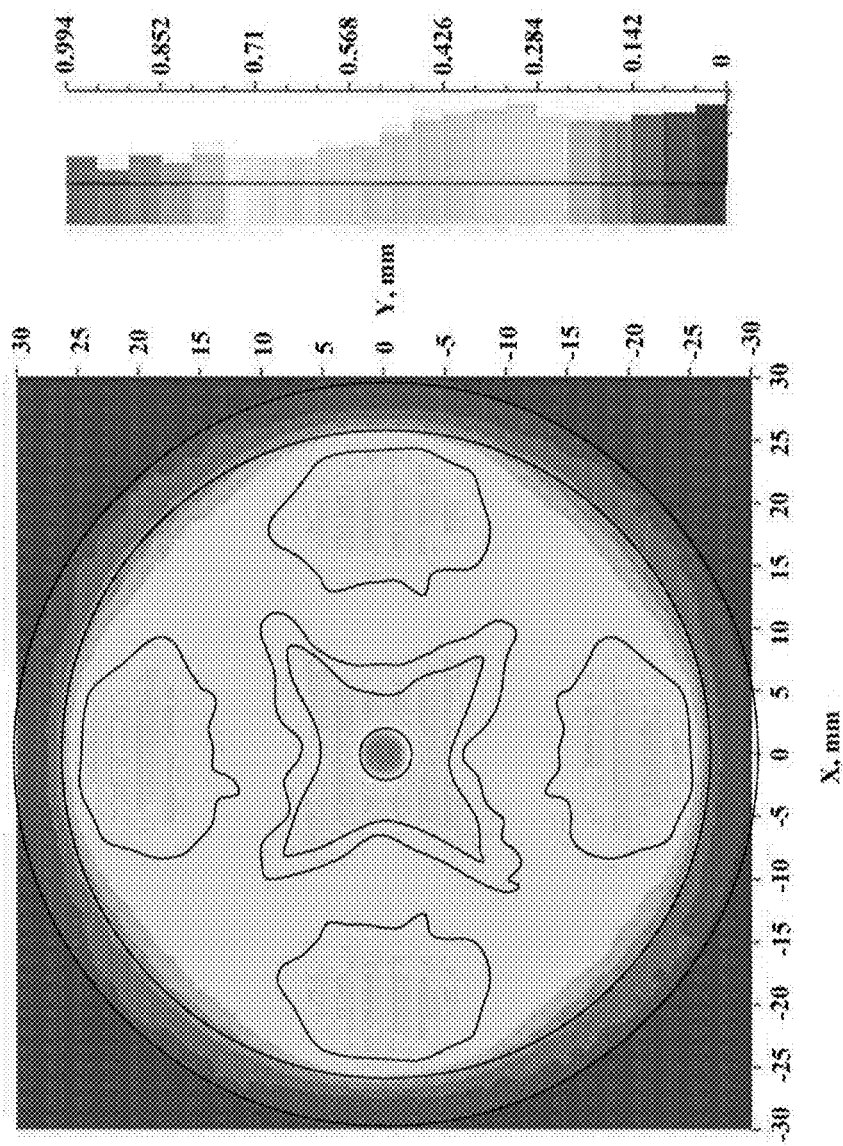
FIG. 17A is a graph depicting intensity distribution of light in use of a sterilizing device according to an embodiment of the present invention.
Figure 17B:
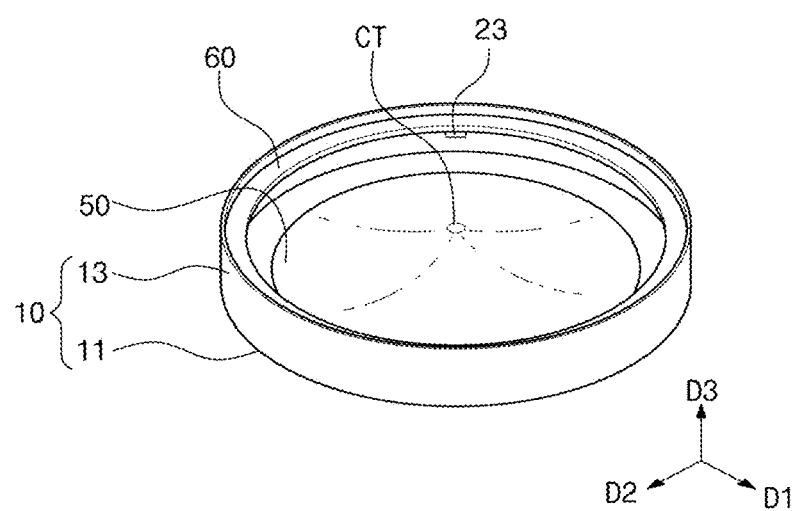
FIG. 17B is a view of some portions of the sterilizing device shown in FIG. 17A.

FIG. 17A is a graph depicting intensity distribution of light in use of a sterilizing device according to an embodiment of the present disclosure and FIG. 17B is a view of some portions of the sterilizing device that corresponds to the graph shown in FIG. 17A. As can be seen from FIG. 17B, in the sterilizing device, the light emitting devices are disposed on the sidewall of the housing, the reflector is disposed on the bottom of the housing, and the blocking portion is further formed on the sidewall. Four (4) light emitting devices are disposed on the sidewall and the reflector 50 covers a portion of the bottom.

Figure 18A:
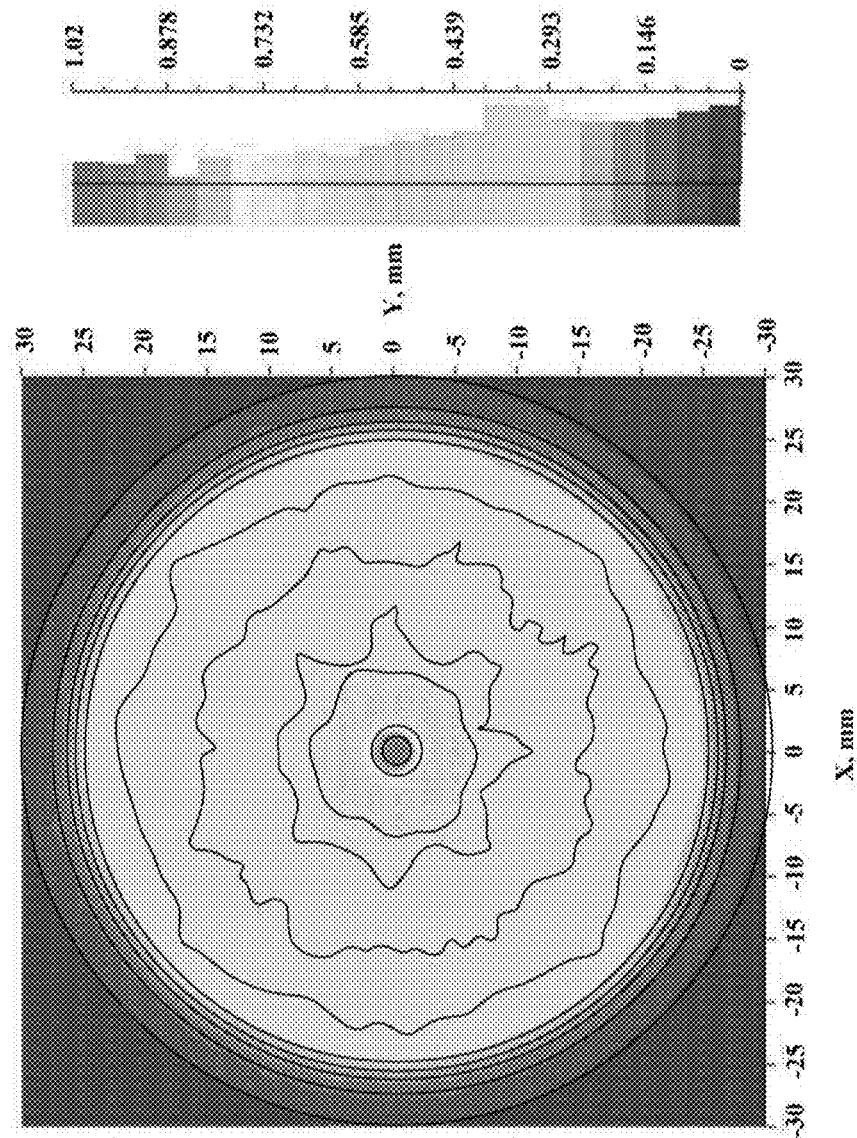
FIG. 18A is a graph depicting intensity distribution of light in use of a sterilizing device according to an embodiment of the present invention.
Figure 18B:
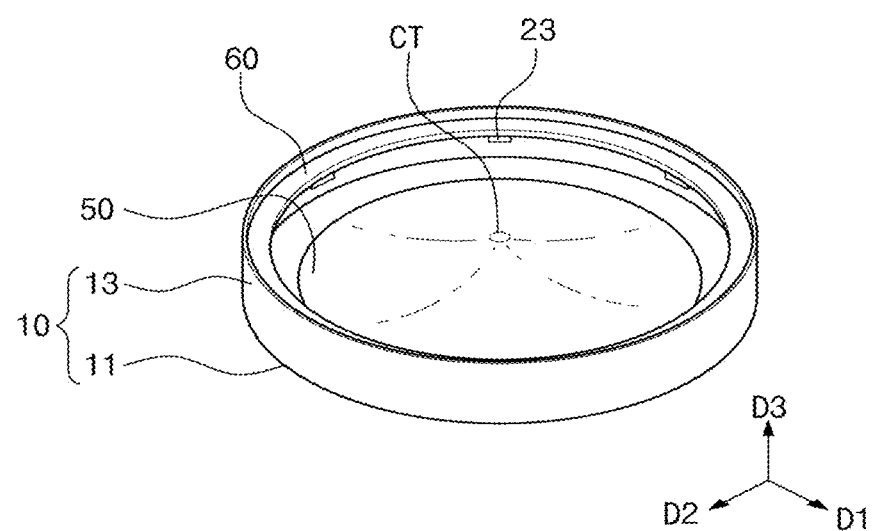
FIG. 18B is a view of some portions of the sterilizing device shown in FIG. 18A.

FIG. 18A is a graph depicting intensity distribution of light in use of a sterilizing device according to an embodiment of the present disclosure and FIG. 18B is a view of some portions of the sterilizing device that corresponds to the graph shown in FIG. 18A. As can be seen from FIG. 18B, in the sterilizing device, the light emitting devices are disposed on the sidewall of the housing, the reflector 50 is disposed on the bottom of the housing, and the blocking portion 60 is further formed on the sidewall. Six (6) light emitting devices are arranged at constant intervals. The reflector covers a portion of the bottom.

Referring to FIG. 13A and FIG. 14A, in the typical sterilizing devices, regions in which the intensity of light is high and regions in which the intensity of light is not high appear clearly. In particular, referring to FIG. 13A, the intensity of light is very high in regions in which four light emitting devices are disposed on the bottom, and is significantly low in other regions in which no light emitting device is disposed. Referring to FIG. 14A, it can be seen that, despite the light emitting devices on the sidewall, the intensity of light is significantly low in regions in which no light emitting device is disposed. Further, in the typical sterilizing devices, the intensity of light is lower in a region corresponding to the center of the light emission region than in a surrounding region.

On the contrary, referring to FIG. 15A, as the reflector is disposed on the bottom, overall uniformity of light is significantly improved, despite higher intensity of light in regions corresponding to the light emitting devices on the sidewall than other regions, and a relatively dark area (that is, a portion at which the intensity of light is significantly low) is remarkably narrowed, as compared with the typical sterilizing devices. In particular, reduction in intensity of light does not clearly appear in the region corresponding to the center of the light emission region.

Furthermore, referring to FIG. 16A, as the reflector is disposed on the bottom, overall uniformity of light is further improved, despite higher intensity of light in regions corresponding to the light emitting devices on the sidewall than other regions. Accordingly, a relatively dark area (that is, a portion at which the intensity of light is significantly low) is remarkably narrowed, as compared with the typical sterilizing devices.

Furthermore, as can be seen from the graph of FIG. 17A in which the blocking portion is disposed to prevent light from traveling in the upward direction, uniformity of light is further improved in the light emission region.

Furthermore, as can be seen from FIG. 18A, uniformity of light is further improved with increasing number of light emitting devices arranged at constant intervals.

As such, the sterilizing device according to the embodiments can provide light at uniform intensity in the light emission region. As a result, the sterilizing device according to the embodiments can effectively treat the fluid flowing in the pipe disposed at an upper side thereof.

With the structure described above, the sterilizing device may be applied to or employed by various apparatuses.

Figure 19:
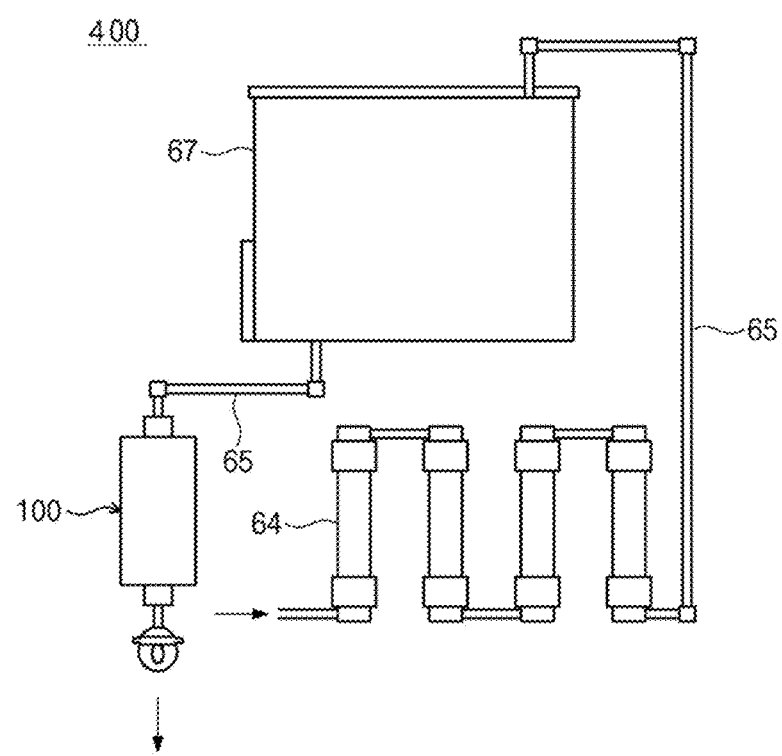
FIG. 19 is a schematic view of a water purifier according to an embodiment of the present invention.

FIG. 19 is a schematic view of a water purifier according to an embodiment of the present invention.

Referring to FIG. 19, the water purifier according to the embodiment includes filters 64 primarily filtering water, a reservoir 67 storing water having passed through the filters 64, and a sterilizing device 100 connected to the reservoir 67.

The filters 64 serve to remove foreign matter from the supplied water. The water purifier may further include a pump (not shown) connected to the filters 64 to supply water to the filters 64. The filters 64 may be provided in various numbers, including filters for removing large impurities, filters for removing heavy metals and bacteria, and the like. In the case of only sterilizing sufficiently purified water using the sterilizing device 100, the filters 64 may be omitted.

Water from which foreign matter is removed by the filters 64 is delivered to the reservoir 67 through a connection tube 65. The water purifier may be provided with at least one reservoir 67 or multiple reservoirs 67. Here, in a structure wherein water to be purified is supplied to the sterilizing device 100, the reservoir 67 may be omitted.

The sterilizing device 400 treats water supplied from the reservoir 67. Here, treatment in the sterilizing device may refer to various measures, such as sterilization, purification, deodorization, and the like, as described above. As shown in FIG. 19, the sterilizing device 400 may be further provided with a draw valve to allow a user to dispense water immediately.

As such, with the sterilizing device according to the present disclosure, it is possible to implement an apparatus having a very simple structure and high effects in treatment of air or water.

Although some embodiments have been described herein, it should be understood that these embodiments are provided for illustration only and are not to be construed in any way as limiting the present invention, and that various modifications, changes, alterations, and equivalents can be made by those skilled in the art without departing from the spirit and scope of the invention. Therefore, the scope of the present invention is not limited to the detailed description herein and should be defined only by the accompanying claims and equivalents thereto.

What is claimed is:

1. A sterilizing device comprising:
   a housing including a bottom and a sidewall extending upwards from the bottom and having an accommodation space defined by the bottom and the sidewall;
   a reflector disposed on the bottom and having a curved reflective surface protruding from the bottom; and
   a light emitting device disposed on the sidewall and emitting light,
   wherein the curved reflective surface has a vertex having a highest height measured from a center of the bottom in plan view;
   wherein, in a cross-section of the curved surface taken along a line perpendicular to the bottom and passing through a center of the bottom, a curved line of the curved reflective surface forms a portion of a parabolic line and a distance from the bottom to a focal point of the parabolic line is greater than a distance from the bottom to a vertex of the curved reflective surface.

2. The sterilizing device according to claim 1, further comprising a support portion disposed on the reflector and having light transmittance.

3. The sterilizing device according to claim 2, wherein the curved surface has a height gradually decreasing from the center of the bottom to an outside of the bottom.

4. The sterilizing device according to claim 1, wherein the reflector has a smaller diameter than a diameter of the bottom.

5. The sterilizing device according to claim 1, wherein the bottom has a greater width than a height of the sidewall.

6. The sterilizing device according to claim 1, wherein the light emitting device is provided in plural and is disposed on the sidewall to emit light into the accommodation space.

7. The sterilizing device according to claim 6, wherein the light emitting devices are arranged at constant intervals in a radial direction.

8. The sterilizing device according to claim 1, further comprising:
   a blocking portion provided to an end of the sidewall distant from the bottom and blocking some of light emitted from the light emitting device.

9. The sterilizing device according to claim 8, wherein the blocking portion is disposed along an edge of the bottom in plan view.

10. The sterilizing device according to claim 1, further comprising:
    a pipe disposed in the housing to be placed on a surface of the housing facing the bottom and adapted to deliver a fluid.

11. The sterilizing device according to claim 10, wherein a distance from the bottom to the focal point of the parabolic line is greater than a distance from the bottom to the pipe.

12. The sterilizing device according to claim 10, wherein at least a part of the pipe is provided in a spiral shape on the surface of the housing facing the bottom.

13. The sterilizing device according to claim 10, wherein at least part of the pipe is transparent.

14. A sterilizing device comprising:
    a housing comprising a bottom and a sidewall extending upwards from the bottom and having an accommodation space defined by the bottom and the sidewall;
    a reflector disposed on the bottom and having a curved reflective surface having a height gradually decreasing from a center of the bottom to an outside of the bottom;
    a support portion disposed on the reflector and having light transmittance;
    a light emitting device disposed on the sidewall and emitting light; and
    a cover fastened to the housing and covering the housing, wherein, in a cross-section of the curved reflective surface, taken along a line perpendicular to the bottom and passing through a center of the bottom, a curved line corresponding to the curved reflective surface forms a portion of a parabolic line and a distance from the bottom to a focal point of the parabolic line is greater than a distance from the bottom to a vertex of the curved reflective surface.

15. The sterilizing device according to claim 14, wherein the light emitting device is disposed to apply the light to at least a portion of a sterilization object to be sterilized by the light with the support portion interposed therebetween.

16. The sterilizing device according to claim 15, wherein the sterilization object is a pipe in which a fluid flows.

17. The sterilizing device according to claim 16, wherein the pipe is disposed in the housing to be placed on a surface of the housing facing the bottom.

18. The sterilizing device according to claim 17, wherein at least one of the housing and the cover has openings corresponding to the inlet and the outlet.

19. The sterilizing device according to claim 15, wherein the curved reflective surface has the vertex having a highest height measured from a center of the bottom in plan view.

20. A water supply comprising:
   a reservoir containing water; and
   a water treatment device connected to the reservoir and treating the water, the water treatment device comprising:
      a housing comprising a bottom and a sidewall extending upwards from the bottom and having an accommodation space defined by the bottom and the sidewall;
      a pipe disposed in the housing to be placed on a surface of the housing facing the bottom and adapted to deliver water;
      a reflector disposed between the bottom and the pipe and having a curved reflective surface protruding from the bottom towards the pipe; and
      a light emitting device disposed on the sidewall and emitting light to the water.

* * * * *